US012053373B2

(12) United States Patent
McLean et al.

(10) Patent No.: US 12,053,373 B2
(45) Date of Patent: Aug. 6, 2024

(54) PROSTHETIC LEAFLET DEVICE

(71) Applicant: Half Moon Medical, Inc., Menlo Park, CA (US)

(72) Inventors: Matt McLean, San Francisco, CA (US); Hanson S. Gifford, III, Woodside, CA (US); James I. Fann, Menlo Park, CA (US); Douglas Sutton, Menlo Park, CA (US)

(73) Assignee: Half Moon Medical, Inc., Menlo Park, CA (US)

( * ) Notice: Subject to any disclaimer, the term of this patent is extended or adjusted under 35 U.S.C. 154(b) by 21 days.

(21) Appl. No.: 17/365,454

(22) Filed: Jul. 1, 2021

(65) Prior Publication Data

US 2022/0125579 A1    Apr. 28, 2022

Related U.S. Application Data

(63) Continuation of application No. 16/044,447, filed on Jul. 24, 2018, now Pat. No. 11,083,572.
(Continued)

(51) Int. Cl.
*A61F 2/24* (2006.01)
*A61F 2/00* (2006.01)

(52) U.S. Cl.
CPC .......... *A61F 2/2412* (2013.01); *A61F 2/0063* (2013.01); *A61F 2/2454* (2013.01);
(Continued)

(58) Field of Classification Search
CPC .................................. A61F 2/24; A61F 2/2496
See application file for complete search history.

(56) References Cited

U.S. PATENT DOCUMENTS 6,869,444 B2    3/2005    Gabbay
7,160,322 B2    1/2007    Gabbay
(Continued)

FOREIGN PATENT DOCUMENTS

EP    2819618 A1    1/2015
EP    3167846 A1    5/2017
(Continued)

OTHER PUBLICATIONS

ISA, PCT Application No. PCT/US2018/043566, International Search Report and Written Opinion mailed Oct. 24, 2018, 14 pages.
(Continued)

*Primary Examiner* — Brian A Dukert
*Assistant Examiner* — Rebecca Lynee Zimmerman
(74) *Attorney, Agent, or Firm* — Perkins Coie LLP

(57) ABSTRACT

A heart valve repair device, comprising an atrial-fixation member having an expandable mesh configured to have oval or circular shape in a deployed configuration, the atrial-fixation member defining a central lumen; and a baffle extending from a portion of the atrial-fixation member, the baffle having an anterior portion with a smooth, atraumatic surface configured to coapt with at least a portion of one or more native leaflets of a native heart valve, a posterior portion configured to engage and displace at least a portion of another native leaflet of the native heart valve, wherein the baffle extends radially inward from the atrial-fixation member into the central lumen to approximate a closed position of the displaced native leaflet.

26 Claims, 28 Drawing Sheets

Related U.S. Application Data

(60) Provisional application No. 62/582,519, filed on Nov. 7, 2017, provisional application No. 62/552,595, filed on Aug. 31, 2017.

(52) U.S. Cl.
CPC ...... *A61F 2/246* (2013.01); *A61F 2002/0068* (2013.01); *A61F 2210/0014* (2013.01); *A61F 2220/0008* (2013.01); *A61F 2220/0025* (2013.01); *A61F 2220/0075* (2013.01); *A61F 2230/0006* (2013.01); *A61F 2230/0008* (2013.01); *A61F 2230/0054* (2013.01)

(56) References Cited

U.S. PATENT DOCUMENTS

| | | | |
|---|---|---|---|
| 9,011,523 B2 | 4/2015 | Sequin | |
| 9,592,118 B2 | 3/2017 | Khairkhahan et al. | |
| 9,592,121 B1 | 3/2017 | Khairkhahan | |
| 9,610,163 B2 | 4/2017 | Khairkhahan et al. | |
| 9,907,652 B2 | 3/2018 | Chau et al. | |
| 10,123,874 B2 | 11/2018 | Khairkhahan et al. | |
| 10,166,098 B2 | 1/2019 | Khairkhahan et al. | |
| 10,390,714 B2 | 8/2019 | Wolinsky et al. | |
| 10,449,046 B2 | 10/2019 | Rafiee | |
| 10,470,883 B2 | 11/2019 | Khairkhahan et al. | |
| 10,478,303 B2 | 11/2019 | Khairkhahan | |
| 10,500,048 B2 | 12/2019 | Khairkhahan et al. | |
| 10,512,542 B2 | 12/2019 | Khairkhahan et al. | |
| 10,702,386 B2 | 7/2020 | Khairkhahan et al. | |
| 11,000,372 B2 | 5/2021 | Khairkhahan et al. | |
| 11,083,572 B2 | 8/2021 | McLean et al. | |
| 11,344,410 B2 | 5/2022 | Hacohen et al. | |
| 2003/0199975 A1* | 10/2003 | Gabbay | A61F 2/2454 623/1.14 |
| 2004/0093060 A1 | 5/2004 | Sequin et al. | |
| 2007/0038297 A1 | 2/2007 | Bobo, Jr. et al. | |
| 2008/0077235 A1 | 3/2008 | Kirson | |
| 2010/0217382 A1 | 8/2010 | Chau et al. | |
| 2010/0262233 A1 | 10/2010 | He | |
| 2010/0280604 A1 | 11/2010 | Zipory et al. | |
| 2011/0029072 A1 | 2/2011 | Gabbay | |
| 2011/0276130 A1 | 11/2011 | Alameddine | |
| 2012/0197388 A1 | 8/2012 | Khairkhahan et al. | |
| 2012/0197392 A1 | 8/2012 | DuMontelle et al. | |
| 2013/0006352 A1 | 1/2013 | Yaron | |
| 2014/0067048 A1 | 3/2014 | Chau et al. | |
| 2014/0358223 A1 | 12/2014 | Rafiee et al. | |
| 2015/0119981 A1 | 4/2015 | Khairkhahan et al. | |
| 2015/0142104 A1 | 5/2015 | Braido | |
| 2015/0148893 A1 | 5/2015 | Braido et al. | |
| 2015/0230919 A1 | 8/2015 | Chau et al. | |
| 2015/0327996 A1 | 11/2015 | Fahim et al. | |
| 2016/0030176 A1 | 2/2016 | Mohl et al. | |
| 2016/0045165 A1 | 2/2016 | Braido et al. | |
| 2016/0045316 A1 | 2/2016 | Braido et al. | |
| 2016/0074164 A1 | 3/2016 | Naor | |
| 2017/0065418 A1 | 3/2017 | Skarsgard | |
| 2017/0095332 A1 | 4/2017 | Bruchman | |
| 2017/0165067 A1* | 6/2017 | Barajas-Torres | A61F 2/2439 |
| 2017/0258589 A1* | 9/2017 | Pham | A61F 2/246 |
| 2017/0296706 A1 | 10/2017 | Simon et al. | |
| 2018/0143087 A1 | 5/2018 | Gouko et al. | |
| 2018/0147054 A1 | 5/2018 | Chau et al. | |
| 2018/0243087 A1 | 8/2018 | Kapadia | |
| 2018/0256318 A1* | 9/2018 | Khairkhahan | A61F 2/2466 |
| 2018/0271651 A1 | 9/2018 | Christianson et al. | |
| 2018/0325666 A1 | 11/2018 | Ma | |
| 2019/0091047 A1 | 3/2019 | Walsh | |
| 2020/0188108 A1 | 6/2020 | Grimm et al. | |
| 2020/0205978 A1 | 7/2020 | Padala et al. | |
| 2020/0222185 A1 | 7/2020 | Kappetein et al. | |
| 2020/0268512 A1 | 8/2020 | Mohl | |
| 2020/0289265 A1 | 9/2020 | Gifford, III et al. | |
| 2020/0360138 A1 | 11/2020 | Ma | |
| 2021/0085462 A1 | 3/2021 | Gifford, III et al. | |
| 2021/0307901 A1 | 10/2021 | Raanani et al. | |
| 2022/0039951 A1 | 2/2022 | Khairkhahan et al. | |
| 2022/0125586 A1 | 4/2022 | Rafiee | |
| 2022/0160508 A1 | 5/2022 | Miyashiro et al. | |
| 2023/0040083 A1 | 2/2023 | Gifford, III et al. | |

FOREIGN PATENT DOCUMENTS

| | | |
|---|---|---|
| JP | 2005535384 A | 11/2005 |
| WO | 2004014258 A1 | 2/2004 |
| WO | 2005002424 A3 | 1/2005 |
| WO | 2012177942 A2 | 12/2012 |
| WO | 2014195422 A1 | 12/2014 |
| WO | 2014207575 A2 | 12/2014 |
| WO | 2015052570 A1 | 4/2015 |
| WO | 2017096157 A1 | 6/2017 |
| WO | 2018142186 A1 | 8/2018 |
| WO | 2019045910 A1 | 3/2019 |
| WO | 2020101676 A1 | 5/2020 |
| WO | 2021027588 A1 | 2/2021 |
| WO | WO2021113449 | 6/2021 |

OTHER PUBLICATIONS

First Office Action, CN Application No. 201880071508.7, mailed Jul. 26, 2022, 8 pages.

Japanese Office Action Application No. 2020-534161, mailed Sep. 5, 2022.

ISA, PCT Application No. PCT/US2022/048999, International Search Report and Written Opinion mailed Mar. 15, 2023, 23 pages.

* cited by examiner

PROSTHETIC LEAFLET DEVICE

CROSS-REFERENCE TO RELATED APPLICATIONS

The present application is a continuation of U.S. patent application Ser. No. 16/044,447, filed Jul. 24, 2018, which claims the benefit of and priority to U.S. Provisional Patent Application No. 62/552,595, file Aug. 31, 2017, and U.S. Provisional Patent Application No. 62/582,519, filed Nov. 7, 2017, the disclosures of which are incorporated herein by reference in their entirety.

FIELD OF THE INVENTION

The present technology relates generally to implants for repairing a regurgitant or incompetent cardiac valve and for methods of implanting the same. The present technology is particularly useful for repairing a regurgitant mitral valve.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are a number of structural factors that may affect the proper closure of the mitral valve leaflets. For example, many patients suffering from heart disease experience dilation of the heart muscle, resulting in an enlarged mitral annulus. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Typically, treatment for mitral valve regurgitation has involved the application of diuretics and/or vasodilators to reduce the amount of blood flowing back into the left atrium. Other procedures have involved surgical approaches (open and intravascular) for either the repair or replacement of the valve. For example, typical repair approaches have involved cinching or resecting portions of the dilated annulus.

Cinching of the annulus has been accomplished by the implantation of annular or peri-annular rings which are generally secured to the annulus or surrounding tissue. Other repair procedures have also involved suturing or clipping of the valve leaflets into partial apposition with one another.

Alternatively, more invasive procedures have involved the replacement of the entire valve itself where mechanical valves or biological tissue are implanted into the heart in place of the mitral valve. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

In addition to its irregular, unpredictable shape, the mitral valve annulus lacks a significant amount of radial support from surrounding tissue. The mitral valve is bound by muscular tissue on the outer wall only. The inner wall of the mitral valve is bound by a thin vessel wall separating the mitral valve annulus from the inferior portion of the aortic outflow tract. As a result, significant radial forces on the mitral annulus could lead to collapse of the inferior portion of the aortic tract with potentially fatal consequences.

The chordae tendineae of the left ventricle may also present an obstacle in deploying a mitral valve repair device. The maze of chordae in the left ventricle makes navigating and positioning a deployment catheter that much more difficult in mitral valve repair.

Given the difficulties associated with current procedures, there remains the need for simple, effective, and less invasive devices and methods for treating dysfunctional heart valves.

SUMMARY OF THE PRESENT TECHNOLOGY

Disclosed is a heart valve repair device, comprising an atrial-fixation member having an expandable mesh configured to have oval or circular shape in a deployed configuration, the atrial-fixation member defining a central lumen; and a baffle extending from a portion of the atrial-fixation member, the baffle having an anterior portion with a smooth, atraumatic surface configured to coapt with at least a portion of one or more native leaflets of a native heart valve, a posterior portion configured to engage and immobilize at least a portion of another native leaflet of the native heart valve, wherein the baffle extends radially inward from the atrial-fixation member into the central lumen to approximate a closed position of the immobilized leaflet.

In the aforementioned device, the baffle having struts configured into a basket having a hollow interior volume, the baffle extending from a portion of the atrial-fixation member, wherein the baffle includes a smooth, atraumatic coaptation surface facing the central lumen which defines a prosthetic coaptation surface for at least a portion of one or more native leaflets, and a restraining portion configured to engage and restrain at least a first portion of a functionally deficient native leaflet while leaving a second portion of the functionally deficient native leaflet mobile, the baffle extends radially inward from the into the central lumen to approximate a closed position for the functionally deficient leaflet.

A device according to any of the preceding further comprising a plurality of frictional elements provided on portions of the atrial-fixation member or the baffle.

The preceding device, wherein the medial and lateral sides of the atrial-fixation member do not include any frictional elements.

A device according to any of the preceding, wherein the baffle comprises plurality of anterior struts and a plurality of posterior struts with gaps interposed between adjacent ones of the anterior and posterior struts.

A device according to any of the preceding, comprising: a fabric covering at least partially surrounding the baffle; and the basket has a mouth which is not covered by the fabric.

A device according to any of the preceding, comprising: a fabric covering at least partially surrounding the baffle; the basket has a mouth which is covered by the fabric.

A device according to any of the preceding, wherein the baffle comprises a biocompatible foam.

A device according to any of the preceding, wherein the anterior portion of the baffle has a convex shape.

A device according to any of the preceding, wherein the posterior portion of the baffle is sized and configured to engage with a central scallop of an anterior or a posterior mitral valve leaflet having three scallops, while leaving the remaining two scallops mobile.

A device according to any of the preceding, further comprising: a first set of plural suture loops circumferentially disposed around the atrial-fixation member, each suture loop of the first set of suture loops having a lumen; and a first suture disposed in the lumen of the suture loops and interconnecting adjacent suture loops; wherein a diameter of the atrial-fixation member is adjusted by cinching the first suture.

A device according to any of the preceding, further comprising: a second set of plural suture loops circumferentially disposed around the baffle, each suture loop of the second set of suture loops having a lumen; and a second suture disposed in the lumen of the suture loops and interconnecting adjacent suture loops; wherein a diameter of the baffle is adjusted by cinching the second suture.

A device according to any of the preceding, further comprising: a third suture loop provided on the baffle, a third suture disposed in the lumen of the third suture loop; wherein the pulling on the third suture displaces the baffle.

A device according to any of the preceding, further comprising at least one fabric segment of fabric attached to and at least partially spanning the atrial-fixation member, wherein the fabric covering facilitates tissue ingrowth.

A device according to any of the preceding, further comprising at least one fabric segment of fabric depending from the distal end of the atrial-fixation member. The device may further comprise a biasing member attached to the at least one fabric segment and biasing the fabric segment away from the central lumen.

The device according to any of the preceding, further comprising a segment of fabric attached to the atrial-fixation member, wherein the fabric covering facilitates tissue ingrowth.

The device according to any of the preceding, wherein the atrial-fixation member comprises at least two rows of cells.

The device according to any of the preceding, wherein: the atrial-fixation member further comprises a row of chevrons; at least two of the chevrons include a through-hole; and a suture threaded through the through-hole; wherein cinching the suture adjusts a diameter of the atrial-fixation member.

The device according to any of the preceding, wherein the atrial-fixation member has a frustoconical shape. The atrial-fixation member may be configured to engage solely with a wall of the atrium. The size of the atrial-fixation member unconstrained by external forces is larger than a size of the atrium in diastole. The device may be fixed relative to the native cardiac valve solely by the atrial-fixation member and the baffle.

The device according to any of the preceding, wherein the proximal end of the anterior side of the atrial-fixation member is offset vertically from the proximal end of the posterior side of the atrial-fixation member.

The device according to any of the preceding, wherein the atrial-fixation member has an asymmetric shape with a length of the anterior side being longer than a length of the posterior side of the atrial-fixation member such that the anterior side of the atrial-fixation member is taller in a vertical direction than the posterior side of the atrial-fixation member.

The device according to any of the preceding, wherein the posterior side of the atrial-fixation member is stiffer than the anterior side of the atrial-fixation member. The atrial-fixation member may include a plurality of interconnected struts forming plural cells, with the struts on the posterior side of the atrial-fixation member being at least one of thicker, wider and/or having narrower gaps between adjacent struts than the struts on the anterior side of the atrial-fixation member.

Also disclosed is a method for repairing a regurgitant cardiac valve in a heart having an atrium having atrial walls, a ventricle having ventricular walls, a cardiac valve having at least two leaflets which have an open position and a closed position, the cardiac valve located at the boundary between the atrium and the ventricle, and an annulus surrounding the cardiac valve, the method comprising: providing a prosthetic leaflet device, including: an atrial-fixation member formed of a stent-like material, the atrial-fixation member defining a central lumen configured to fluidically couple the atrium and the ventricle, the atrial-fixation member having an anterior portion, a posterior portion, a proximal end, a distal end, a medial side, and a lateral side; and a baffle depending from a distal end of the posterior portion of the atrial-fixation member, an anterior portion of the baffle having a smooth, atraumatic surface which acts as a new coaptation surface for one of the two or more leaflets, a posterior portion of the baffle configured to engage and immobilize at least a portion of another of the two or more leaflets, the baffle protruding into the central lumen and approximating the closed position for the immobilized leaflet; and implanting the prosthetic leaflet device in the atrium such that the anterior, medial and lateral portions of the atrial-fixation member are spaced away from the annulus; and positioning the baffle to abut one of the at least two leaflets.

In the preceding method, the atrial-fixation member of the prosthetic leaflet device may include at least two suture loops having an eyelet, a suture strand threaded through the eyelets, wherein cinching the suture strand collapses the atrial-fixation member; and the step of implanting the leaflet prosthetic includes the steps of: cinching the suture strand to collapse the atrial-fixation member; placing the prosthetic leaflet device with the atrial-fixation member collapsed in the atrium; and uncinching the prosthetic leaflet device such that the atrial-fixation member expands into contact with the atrial walls.

In the preceding method, the prosthetic leaflet device may be fixed relative to the cardiac valve solely by the atrial-fixation member and the baffle.

Also disclosed is a heart valve repair device, comprising: an atrial fixation member defining a central lumen, the atrial fixation member; a baffle attached to the atrial fixation member, the baffle having an anterior portion with a smooth, atraumatic surface defining a prosthetic coaptation surface configured to coapt with at least one native leaflet of a native heart valve, and a posterior portion configured to engage and restrain at least a portion of a functionally deficient leaflet, the baffle extending radially inward into the central lumen to approximate a closed position of the functionally deficient leaflet. The device may further comprise a fabric covering at least partially surrounding the baffle. The baffle may comprise a biocompatible foam. The device may further comprise a plurality of frictional elements provided on the semi-circular ring and on a posterior portion of the baffle. The baffle may form a basket with a hollow interior. The baffle may comprise a plurality of anterior struts and a plurality of posterior struts with gaps interposed between adjacent ones of the anterior and posterior struts. The basket may have a mouth, the basket being covered by a fabric, with the mouth of the basket being uncovered. The anterior portion of the baffle may have a convex shape. The posterior portion of the baffle is sized and configured to engage with a central scallop of an anterior or a posterior mitral valve leaflet having three scallops, while leaving the remaining two scallops mobile. Alternatively, the posterior portion of the baffle is sized and configured to engage with the entire valve leaflet. The atrial fixation member may comprise a semicircular ring extending in a first plane and the baffle extends in a second plane which is parallel and vertically offset from the first plane. The anterior portion of the baffle comprises a biocompatible foam. The atrial fixation member may include a semi-circular ring sized to skirt the periphery of the annulus between the anterolateral commissure and a posteromedial commissure.

Also disclosed is heart valve repair device, comprising: an atrial fixation member defining a central lumen; at least one fixation mechanism having a trigonal anchor system and posterior hook; wherein the trigonal anchor system comprises a first trigonal extension attached to the first end of the partial ring and extending away from the baffle, a second trigonal extension attached to the second end of the partial ring and extending away from the baffle, and one of an anchor and an atraumatic tip attached to a terminal end of the first and second trigonal extensions; wherein the posterior hook is attached to a posterior portion of the atrial fixation member, and the posterior hook has a first portion which extends distally and a second portion which curves in a posterior direction, whereby the posterior hook is configured to extend into the ventricle and engage a ventricular side of a native cardiac annulus; and a baffle attached to the partial ring, the baffle having an anterior portion with a smooth, atraumatic surface which defines a prosthetic coaptation surface for one or more native leaflets, and a posterior portion configured to engage and displace at least a portion of a functionally deficient leaflet, the baffle extending into the central lumen and approximating a closed position for the displaced leaflet.

The preceding device, further comprising a fabric covering at least partially surrounding the baffle. The preceding device, wherein the baffle comprises a biocompatible foam. The preceding device, further comprising a plurality of frictional elements provided on the atrial fixation member and on a posterior portion of the baffle. In any of the preceding devices, the baffle may be a basket with a hollow interior. The baffle comprises a plurality of anterior struts and a plurality of posterior struts with gaps interposed between adjacent ones of the anterior and posterior struts. The basket has a mouth, the basket being covered by a fabric, with the mouth of the basket being uncovered.

In any of the preceding devices, the anterior portion of the baffle may have a convex shape. The posterior portion of the baffle is sized and configured to engage with and immobilize a central scallop of an anterior or a posterior mitral valve leaflet having three scallops, while leaving the remaining two scallops mobile. The posterior portion of the baffle is sized and configured to engage with the entire valve leaflet. The atrial fixation member includes a semi-circular ring sized to skirt the periphery of the native cardiac annulus between an anterolateral commissure and a posteromedial commissure.

Disclosed is a heart valve repair device, comprising: an atrial-fixation member defining a central lumen, the atrial-fixation member; and a baffle attached to the atrial-fixation member, the baffle having an anterior portion with a smooth, atraumatic surface which defines a coaptation surface configured to engage one or more native leaflets, and a posterior portion configured to engage and displace at least a portion of a functionally deficient leaflet, the baffle extending into the central lumen to approximate a closed position for the functionally deficient leaflet.

The previously described device further comprising a fabric covering at least partially surrounding the baffle. The baffle may comprise a biocompatible foam. The device further comprising a plurality of frictional engagement elements provided on the atrial-fixation member and the posterior portion of the baffle. The baffle may be a basket with a hollow interior. The baffle comprises a plurality of anterior struts and a plurality of posterior struts with gaps interposed between adjacent ones of the anterior and posterior struts. The basket has a mouth, the basket being covered by a fabric, with the mouth of the basket being uncovered.

The previously described device wherein the anterior portion of the baffle has a convex shape. The posterior portion of the baffle is sized and configured to engage with and displace a central scallop of an anterior or a posterior mitral valve leaflet having three scallops, while leaving the remaining two scallops mobile. The atrial fixation member includes a partially-circular, frustoconical shaped member having first and second ends, and a brace extending between the first and second ends of the atrial-fixation member.

Any of the previously described devices further comprising at least one fixation mechanism selected from the group (trigonal anchor and posterior hook), wherein the trigonal anchor comprises a first trigonal extension attached to the first end of the atrial-fixation member and extending away from the baffle, a second trigonal extension attached to the second end of the atrial-fixation member and extending away from the baffle, and one of an anchor and an atraumatic tip attached to a terminal end of the first and second trigonal extensions.

Also disclosed is a heart valve repair device for repairing a mitral valve having an anterior leaflet and a posterior leaflet, comprising: an atrial-fixation member configured to have a collapsed configuration and an expanded configuration, the atrial-fixation member having an expandable ring-shaped mesh, and the atrial-fixation member being configured to contact tissue of an atrial wall upstream of a native valve annulus; and a baffle extending radially inwardly from the atrial-fixation member, the baffle having an outer portion configured to displace the posterior leaflet toward a ventricular wall and restrain the posterior leaflet in an open position, an inner portion having a coaptation surface radially inward of the outer portion, wherein the inner portion is spaced apart from the outer portion by a distance such that the coaptation surface is positioned at least proximate a closed position of the anterior leaflet. The atrial-fixation member may be configured to contact only atrial wall tissue above the native valve annulus. The heart valve repair device may further include a biocompatible covering on a surface of the baffle. The baffle may include posterior struts extending in a downstream direction from the atrial-fixation member and anterior struts projecting inwardly and upwardly from a downstream end of the posterior struts, and wherein the heart valve repair device further includes a covering attached to the posterior and anterior struts. The atrial-fixation member may include a plurality of struts, and wherein the heart valve repair device further includes a covering attached to the struts of the atrial-fixation member.

DETAILED DESCRIPTION

Disclosed are various embodiments for addressing a regurgitant or incompetent cardiac valve including but not limited to a mitral valve. Although several examples of prosthetic leaflet devices are disclosed, all share a common theme of displacing at least a portion of at least one valve leaflet and providing a prosthetic, atraumatic coaptation surface for the remaining valve leaflet(s). The prosthetic coaptation surface does not move like a native leaflet in that it does not shift between an open and a closed position. Instead, the prosthetic coaptation surface can be fixed in a position or have limited movement that mimics or approximates the closed position of the partially or completely displaced native leaflet. Several embodiments of valve repair devices are described herein with reference to the mitral valve with the understanding that the utility of the present technology is not limited to the mitral valve and may be used with other heart valves.

Figure 1:
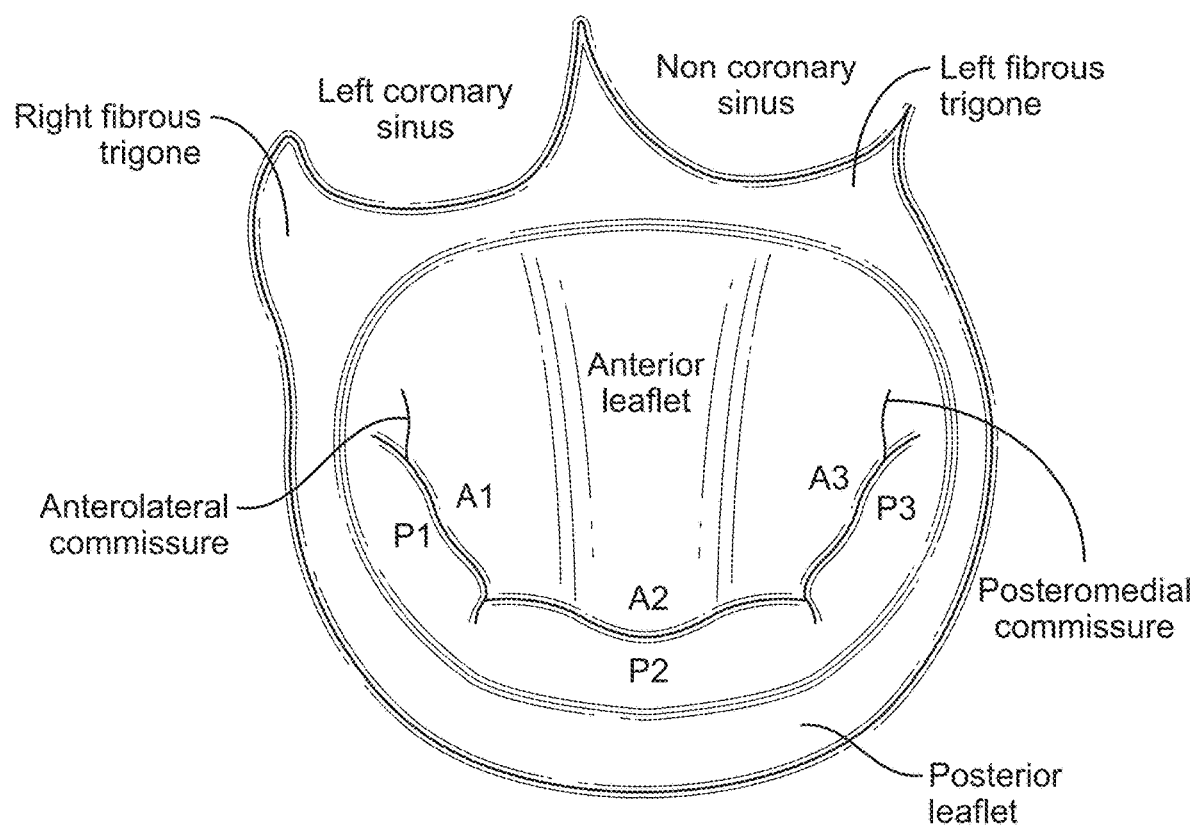
FIG. 1 is a diagram of a mitral valve.

In the context of a mitral valve, the embodiments of the present technology may be used to displace and at least partially displace a portion of one of the leaflets while providing an atraumatic coaptation surface for the other native leaflet. Embodiments of the present technology displace a native leaflet with an implant which occludes approximately the same area as the fully closed native leaflet which is being replaced. The new coaptation surface mimics or approximates the closed position of the native leaflet. Referring to FIG. 1 which, illustrates a native mitral valve, the anterior and posterior leaflets of the mitral valve each have three well-defined scallops (A1-A3 and P1-P3). Some of the embodiments disclosed herein may displace and immobilize only one or two of the leaflet scallops while leaving the remaining leaflet scallops intact and mobile, but other embodiments can displace and immobilize an entire leaflet (i.e., all three scallops) while leaving the opposing leaflet intact and mobile. To simplify the description, several aspects of the present technology are described with respect to displacing and immobilizing the posterior leaflet of a mitral valve while providing an atraumatic coaptation surface for the anterior leaflet. However, the present technology could be used to displace and immobilize the anterior leaflet while providing an atraumatic coaptation surface for the posterior leaflet.

Referring still to FIG. 1, the mitral valve has an anterior leaflet and a posterior leaflet. The anterior leaflet has a semi-circular shape and attaches to two-fifths of the annular circumference. The motion of the anterior leaflet defines a boundary between the inflow (diastole) and outflow (systole) tracts of the left ventricle. The posterior leaflet of the mitral valve has a crescent shape and is attached to approximately three-fifths of the annular circumference. The posterior leaflet typically has two well-defined indentations which divide the leaflet into three individual scallops identified as P1 (anterior or lateral scallop), P2 (middle scallop), and P3 (posterior or medial scallop). The three corresponding segments of the anterior leaflet are A1 (anterior segment), A2 (middle segment), and A3 (posterior segment). The leaflet indentations aid in posterior leaflet opening during diastole.

The mitral valve has anterolateral and posteromedial commissures which define a distinct area where the anterior and posterior leaflets come together at their insertion into the annulus. The commissures may exist as well-defined leaflet segments, but more often this area is a subtle structure that can be identified using two anatomic landmarks: (a) the axis of corresponding papillary muscles, and (b) the commissural chordae, which have a specific fan-like configuration. Several millimeters of valvular tissue separate the free edge of the commissures from the annulus.

The mitral valve is an atrio-ventricular valve fluidically coupling the left atrium to the left ventricle. The mitral annulus defines the anatomical junction between the left ventricle and the left atrium. The fixed end of the leaflets is attached to the annulus. The anterior portion of the mitral annulus is attached to the fibrous trigones and is generally more developed than the posterior annulus. The right fibrous trigone is a dense junctional area between the mitral, tricuspid, non-coronary cusp of the aortic annuli and the membranous septum. The left fibrous trigone is situated at the junction of both left fibrous borders of the aortic and the mitral valve.

The mitral annulus is less well developed at the insertion site of the posterior leaflet as this segment is not attached to any fibrous structures and the fibrous skeleton in this region is discontinuous. The circumference of the posterior portion of the annulus may increase and lead to mitral regurgitation in association with left atrial or left ventricular dilation. The mitral annulus is saddle shaped, and during systole the commissural areas move in the direction of the atrium to make it more planar, while annular contraction also narrows the circumference. Both processes aid in leaflet coaptation and may be affected by processes such as annular dilatation and calcification. The mitral annulus is surrounded by several important anatomic structures, including the aortic valve, the coronary sinus, and the circumflex artery.

FIGS. 2A-2E show a valve repair device in accordance with the present technology. The valve repair device can be a prosthetic leaflet device 100 having an atrial-fixation member 102 and a baffle 114 depending in a downstream direction from the atrial-fixation member 102. The atrial-fixation member 102 can be configured to help position and hold the baffle 114 at a desired location with respect to the native valve anatomy, and the baffle 114 is configured to displace at least a portion of a native leaflet of the valve and create a prosthetic coaptation surface for at least a portion of one or more of the other leaflets of the native valve in the position provided by the atrial-fixation member 102. The baffle 114, for example, can be configured to displace a functionally deficient native leaflet, such as a posterior leaflet which is degenerated, torn, flailing, or otherwise no longer closing effectively during systole. In a valve with a dilated annulus such that regurgitant flow occurs between two native leaflets which no longer coapt effectively, the baffle 114 can extend beyond the dimensions of the existing leaflet to re-establish effective coaptation with the other leaflet(s).

Figure 2A:
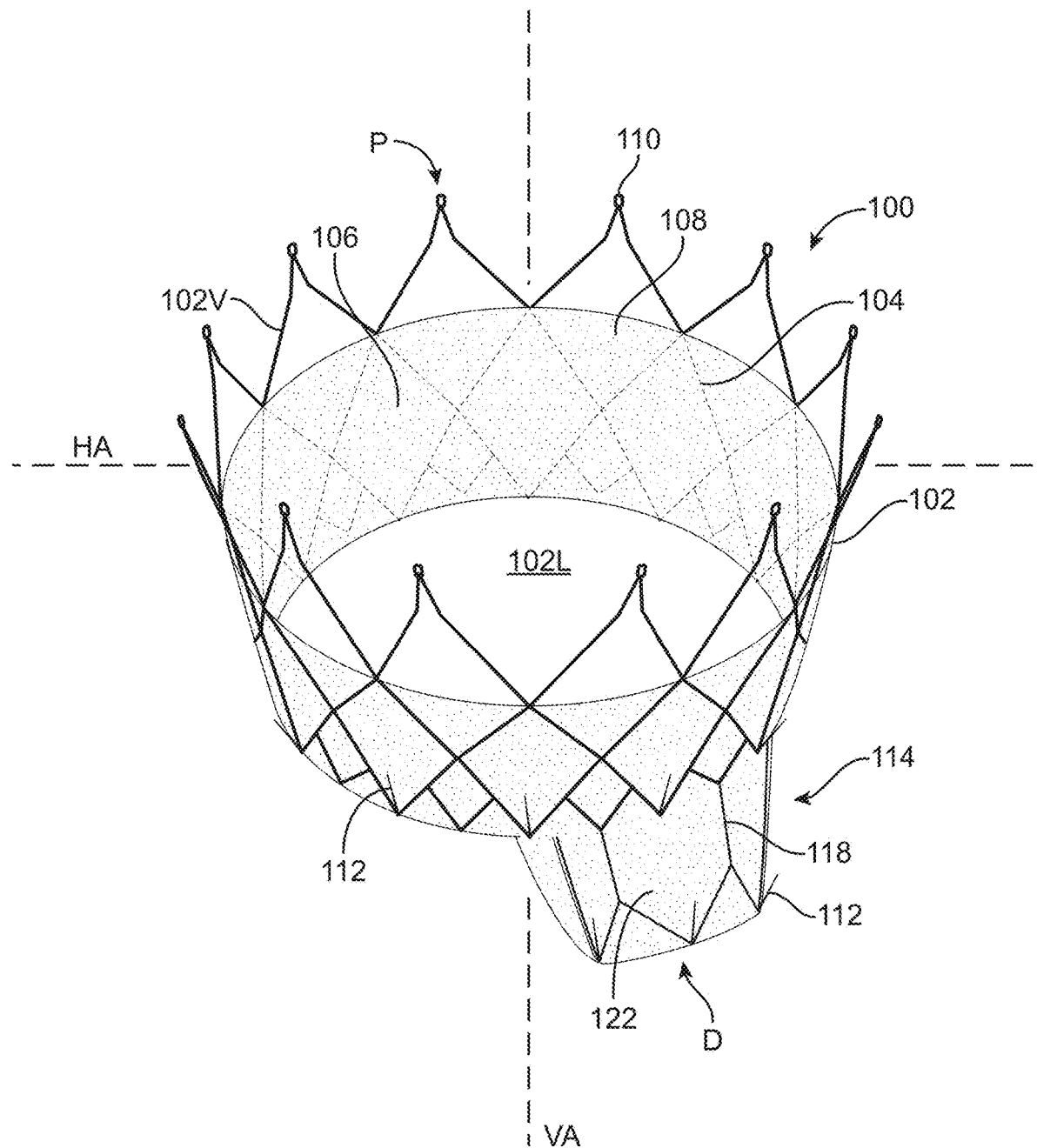
FIGS. 2A-2I are views of a prosthetic leaflet device in accordance with embodiments of the present technology.

The atrial-fixation member 102 can be formed of a mesh, such as a braid or stent-like structure, including a plurality of interconnected wires or struts 104 which cooperatively define a plurality of cells. The atrial-fixation member 102 aids in holding the baffle 114 in place by engaging the walls of the left atrium, and it may have a generally frustoconical shape. Each cell of the atrial-fixation member 102 defines an opening or through hole 106. The unconstrained shape of the atrial-fixation member 102 may be generally circular or oval shaped. The atrial-fixation member 102 can have any number of through holes 106 or any shape or size such that the atrial-fixation member 102 contacts the left atrial wall with at least a threshold amount of radial force to stabilize the position of the baffle 114. The radial force may be adjusted by varying the shape and dimensions of the struts (thickness, width, and spacing between struts) and the shape and dimensions of the through holes 106. For example, wider and/or thicker struts 104 may increase the crush resistance, while larger openings or through holes 106 and/or thinner struts 104 may decrease the crush resistance. These concepts will be discussed in further detail below. In FIG. 2A, openings 106 are generally diamond-shaped.

The atrial-fixation member 102 may be formed of any biocompatible material such as stainless steel, a nickel-titanium alloy or a polymer. The atrial-fixation member 102 could be an elastic self-expanding material or a balloon-expandable material. According to a presently preferred embodiment, the atrial-fixation member 102 is formed of a super-elastic nickel-titanium alloy, e.g. Nitinol®, that is self-expanding.

The prosthetic leaflet device 100 has a vertical axis VA in the direction of blood flow from the atrium to the ventricle and a horizontal axis HA orthogonal to the vertical axis. The prosthetic leaflet device 100 has a proximal side P and a distal side D. The prosthetic leaflet device has a proximal or leading end which faces the atrium and a distal or trailing end which faces the ventricle.

The atrial-fixation member 102 encircles or otherwise defines a lumen 102L which when expanded spans a portion of the left atrium. The atrial-fixation member 102 may be covered in whole or in part by an optional biocompatible covering 108. The biocompatible covering 108 may facilitate sealing and/or tissue ingrowth which may assist in long-term fixation of the device 100. The optional biocompatible covering 108 on the atrial-fixation member 102 may be continuous with or without openings or windows, or it can be discontinuous with discrete sections such that gaps or uncovered portions of the atrial-fixation member 102 are interposed between covered portions. The biocompatible covering 108 may be a fabric formed of a polymer or biomaterial (Polyethylene terephthalate (PET), expanded polytetrafluoroethylene (ePTFE), silicone, urethane, pericardium, etc.). The covering 108 may be attached to the atrial-fixation member 102 by any conventional means including sutures, adhesives, sintering or the like. The covering 108 can be sutured to the inner surface of the atrial-fixation member 102, i.e. the surface of the atrial-fixation member which faces the lumen 102L. Alternatively, the covering 108 may be attached to the outer surface of the atrial-fixation member 102, i.e., the side facing away from the lumen 102L, which in use is the side facing the atrial wall.

The atrial-fixation member 102 is constructed and shaped to atraumatically provide sufficient fixation of the prosthetic leaflet device 100 in the left atrium and to enable delivery, positioning, and retrieval of the device. In the embodiment shown in FIGS. 2A-2C, the uppermost row of struts of the atrial-fixation member 102 form a plurality of inverted V-shaped structures or crown points (e.g., chevrons) 102V. One or more of the chevrons 102V may each include an eyelet 110 at the apex of the inverted V-shaped crown points. The eyelets 110 are sized to receive suture strands (not illustrated) used to deliver, orient and retrieve the prosthetic leaflet device 100 to/from the delivery catheter (not illustrated). The chevrons 102V may extend generally vertically (parallel to the vertical axis VA) or they may be angled toward the lumen 102L to minimize any trauma to the atrial wall, whereas the rest of the atrial-fixation member 102 diverges outwardly (e.g., away from the lumen 102L) to have a frustoconical shape. The chevrons 102V can be angled toward the lumen 102L.

The prosthetic leaflet device 100 shown in FIGS. 2A-2E relies on atrial fixation to hold the device in place. The unconstrained size of atrial-fixation member 102 may be somewhat oversized relative to the size of the atrium in diastole to ensure that the prosthetic leaflet device 100 remains in its desired position. The atrial-fixation member 102 is configured to sit above the mitral valve annulus so that it does not affect the function of the other leaflets of the valve. The atrial-fixation member 102 may include a plurality of frictional engagement portions or cleats 112 which are adapted to frictionally engage, i.e., tent into the tissue without piercing into the tissue of the atrial wall. However, the cleats 112 may have sharpened tips or barbs configured to pierce into the atrial wall. The cleats 112 may be integrally formed with the struts 104 or otherwise attached to the struts 104. The cleats 112 may extend (a) toward the eyelets 110 (i.e., opposite the direction of blood flow, such as upwards, proximally, towards the top of the atrium, or away from the ventricle in mitral valve applications), (b) laterally directly into the walls of the atrium, and/or (c) downwards away from the eyelets 110 (in the direction of blood flow, or downward, distally, toward the ventricle, or away from the atrium in mitral valve applications), or they may extend in multiple directions. The cleats 112 may be provided around the full perimeter of the atrial-fixation member 102, or the cleats 112 may be provided only on portions of the atrial-fixation member 102. For example, the cleats 112 may be provided on the anterior and posterior segments of the atrial-fixation member 102 and not on the lateral segments of the atrial-fixation member 102. The prosthetic leaflet device 100 may rely on atrial fixation using the cleats 112 and/or oversizing of the atrial-fixation member 102 relative to the atrium to hold the prosthetic leaflet device 100 in place. The atrial-fixation member 102 is configured to sit slightly (e.g., 1-10 mm) above the annulus such that, with exception of the baffle 114, the prosthetic leaflet device 100 does not attach to the annulus.

The baffle 114 extends distally (e.g., in the direction of blood flow) from the posterior portion of the atrial-fixation member 102. The baffle 114 provides a prosthetic coaptation surface for the anterior leaflet, and it displaces a native leaflet which is damaged or otherwise does not sufficiently coapt with the anterior leaflet. See FIG. 2D-1. The baffle 114 can be shaped to provide these functions while enhancing or otherwise enabling coaptation with the other leaflets and enhancing blood flow around the baffle. The baffle 114 may, for example, have a teardrop shape, tapering as it extends upwards from a bulbous coaptation surface towards the posterior wall of the left atrium. (See, e.g., FIG. 3E)

The baffle 114 can be integral with the atrial-fixation member 102 such that it is manufactured from the same metal frame. The baffle 114 may alternatively be manufactured from a separate element and connected to a portion of the atrial-fixation member 102, for example, by struts on the baffle 114 or the atrial-fixation member 102.

In some embodiments, the baffle 114 can be formed of a biocompatible foam which is attached to the atrial-fixation member 102. The baffle 114 can alternatively have an adjustable shape to enhance sealing with other leaflets, such as a baffle 114 comprising an inflatable bladder attached to atrial-fixation member 102.

The baffle 114 can also contribute to fixation of the prosthetic leaflet device 100. The posterior portion of the baffle 114 may include frictional elements, such as cleats 112, configured to engage with the posterior leaflet and/or the annulus. The posterior portion of baffle 114 can also be shaped to engage the geometry of the annulus, ventricular wall, and atrial wall. For example, the posterior portion of baffle 114 can have a concave shape from the atrial end to the ventricular end, to engage the annulus and thereby prevent migration in an atrial or ventricular direction.

Figure 2B:
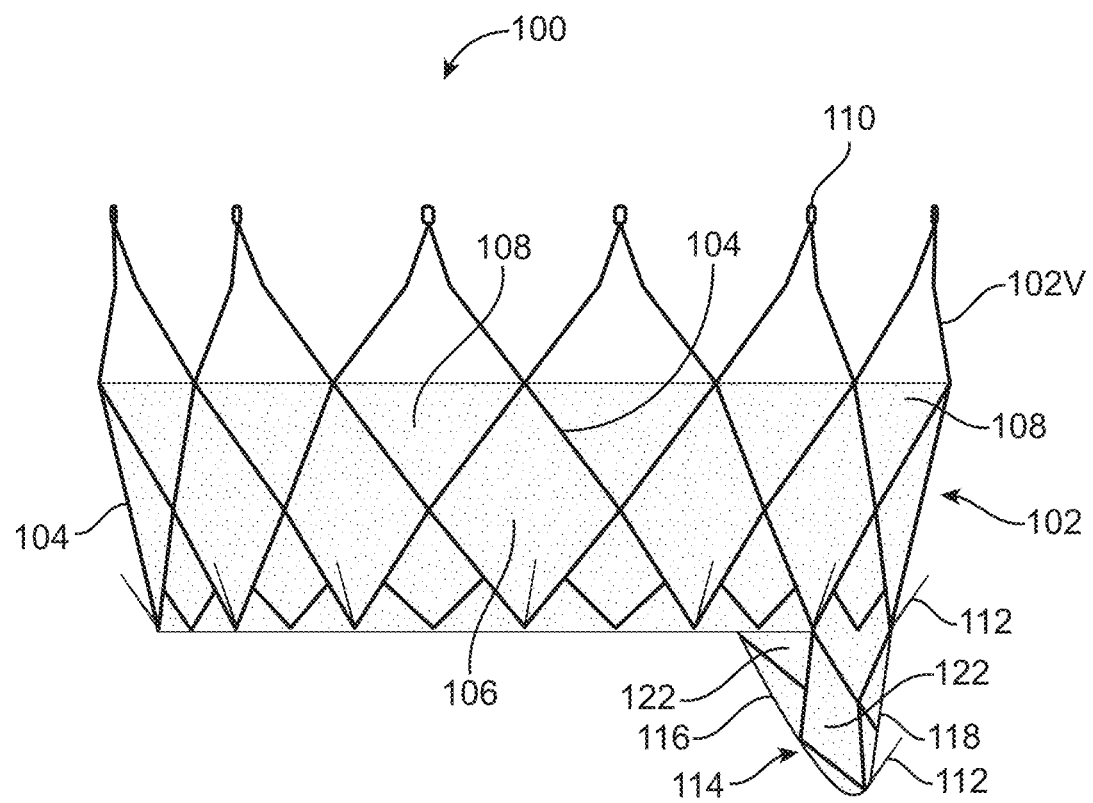
Figure 2C:
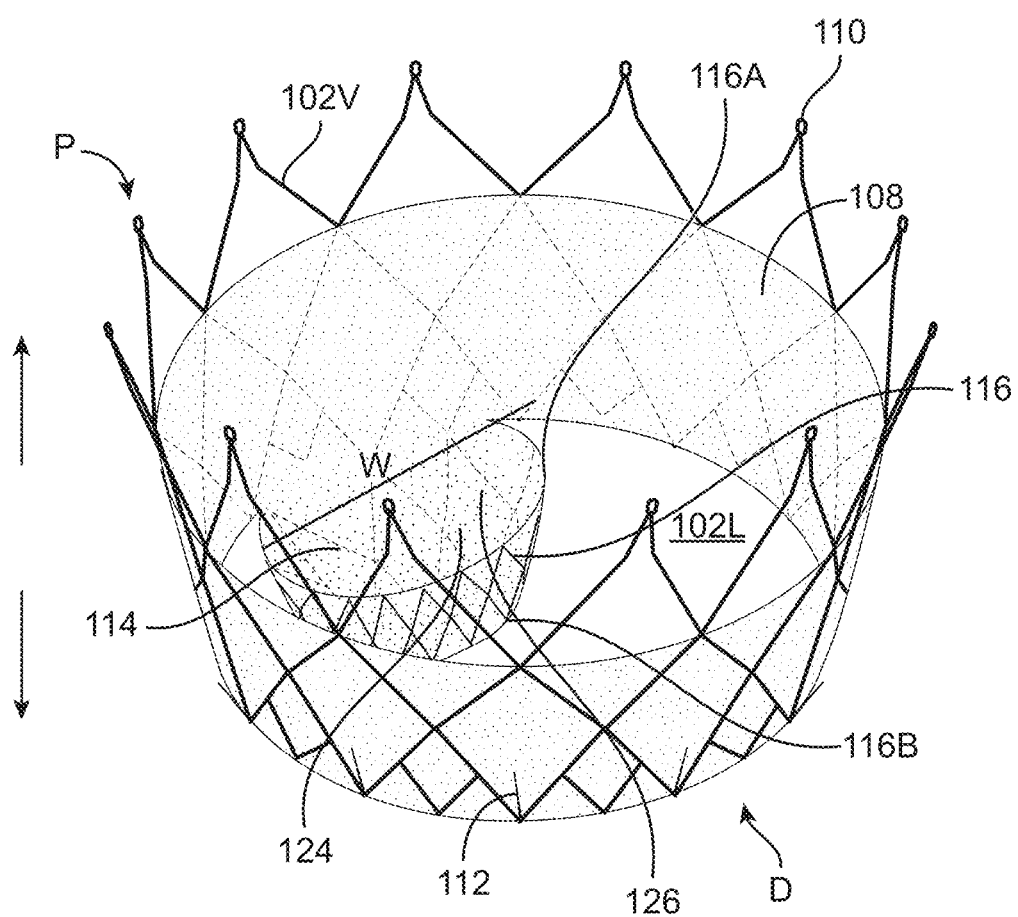
Figures 1, 2D:
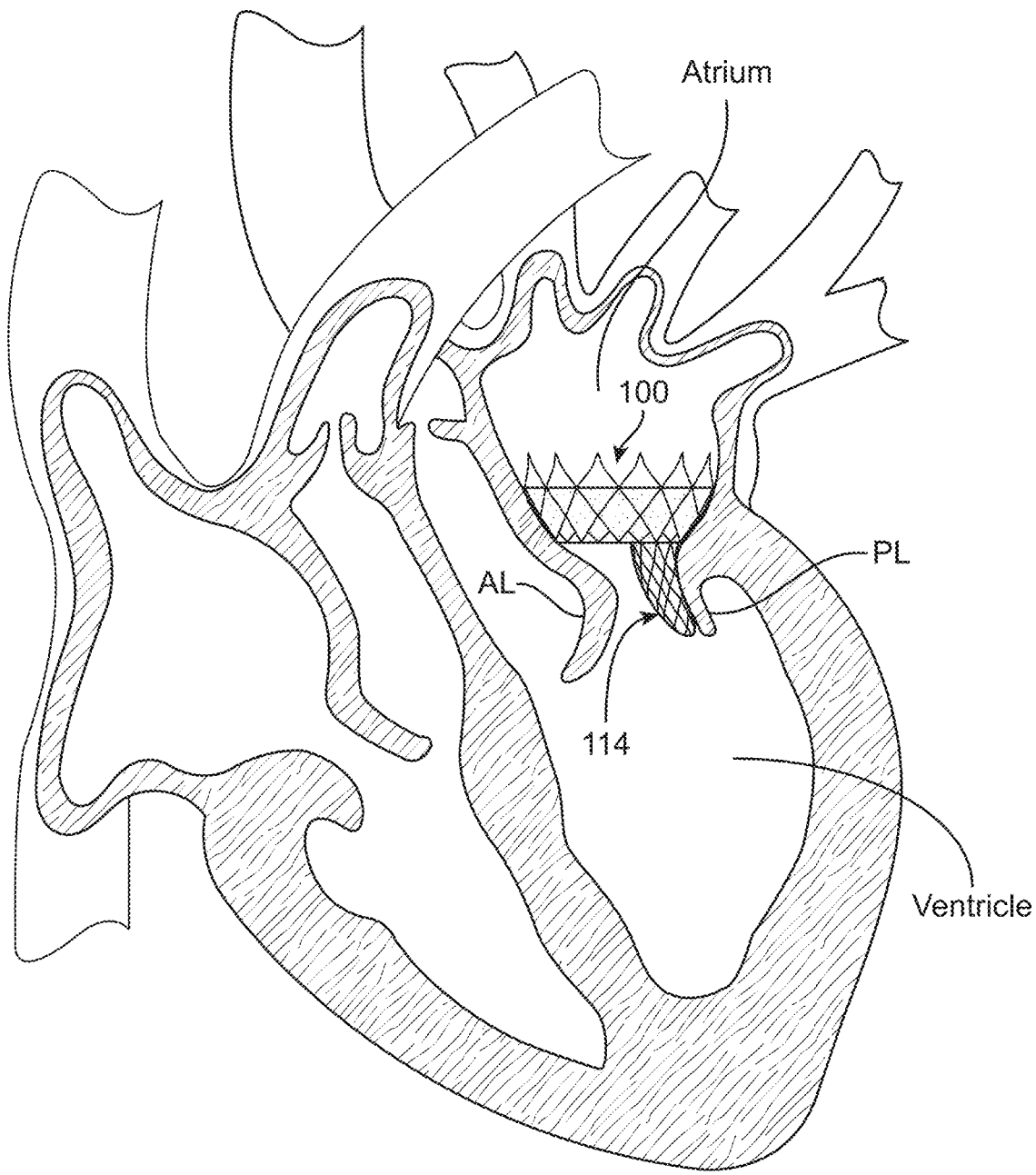
Figures 2, 2D:
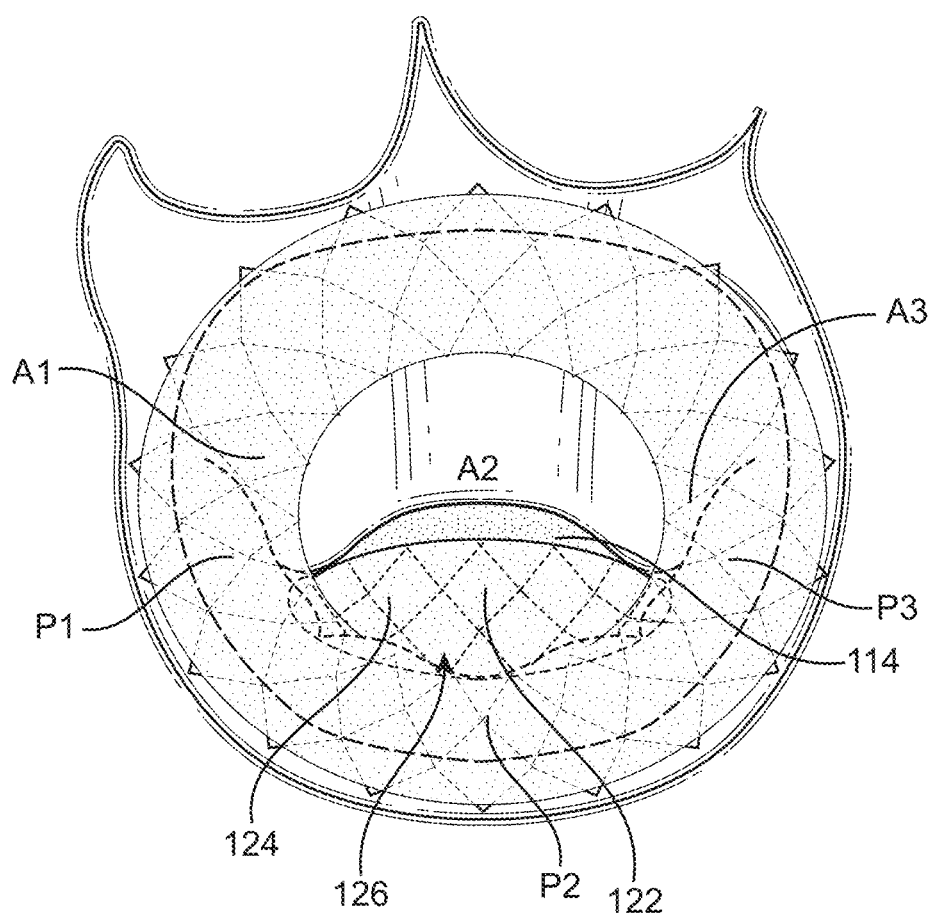
Figures 1, 2E:
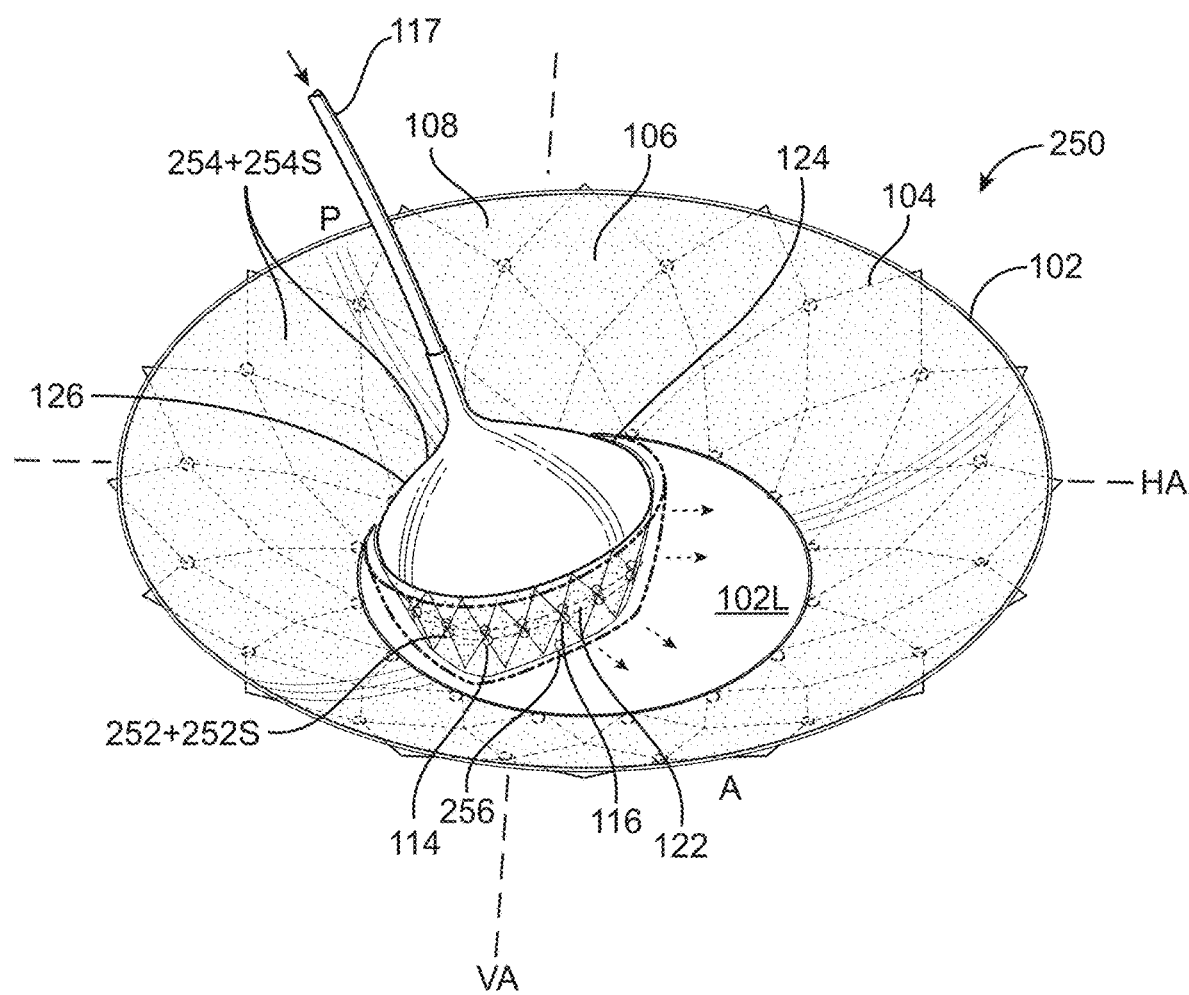
Figures 2, 2E:
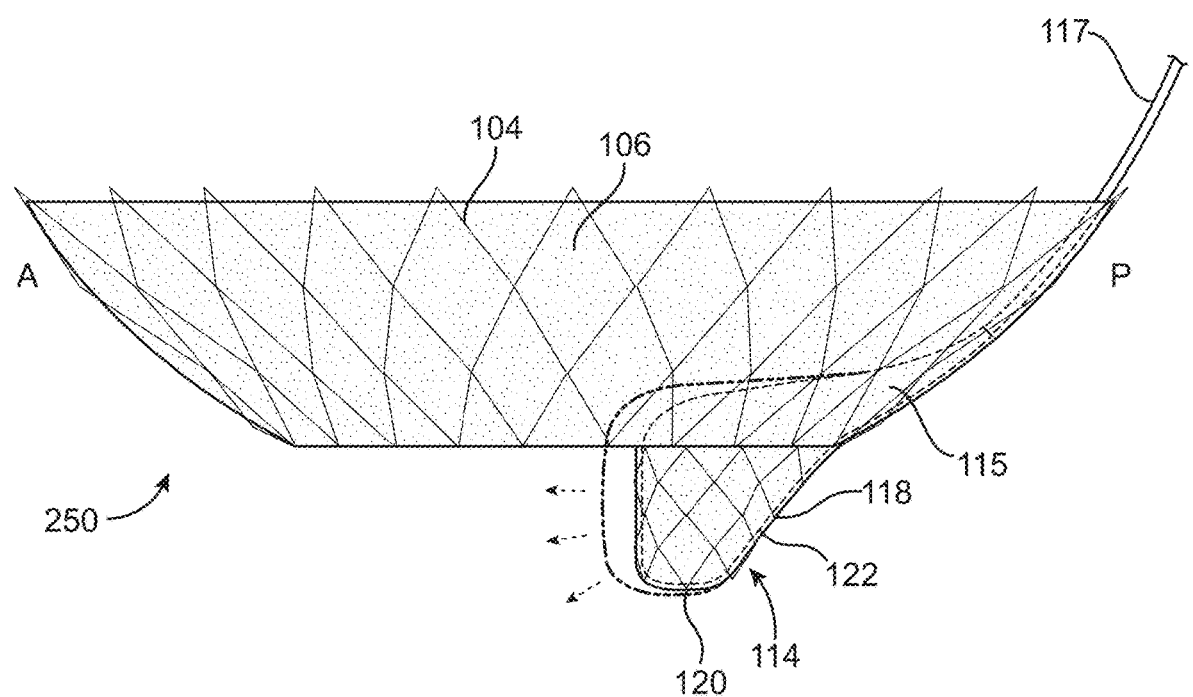

Referring to FIGS. 2A-2C, the baffle 114 can have a basket-like shape encompassing or surrounding a hollow interior. The basket-shaped baffle 114 may include anterior struts 116 (FIGS. 2B and 2C) connected to posterior struts 118 (FIGS. 2A and 2C) by a bridging portion 120 (FIG. 2E-2). A bio-compatible covering 122, which may be the same material used for covering 108, is attached to the baffle 114 to provide a fluid-tight seal with the adjacent leaflets of the valve. The anterior struts 116 may be connected to or integrally formed with the bridging portion 120 and the posterior struts 118, for example from a single tubular mesh. In this embodiment, the baffle 114 is the only portion of the prosthetic leaflet device 100 which traverses the annulus and extends into the ventricle. See, FIG. 2D.

The baffle 114 may take a variety of shapes to facilitate coaptation with the posterior wall and adjacent leaflets and to ensure proper closure of the valve, optimize blood flow to prevent turbulent flow and/or formation of blood clots. The baffle 114 may also be configured to optimize stability of the baffle 114 throughout the cardiac cycle, and for ease of deployment and retrieval. In many embodiments, the anterior struts 116 protrude into the lumen 102L and have a convex shape configured to provide an atraumatic coaptation surface for the anterior leaflet AL. (See, e.g., FIG. 2E.)

The anterior struts 116 span a width W (orthogonal to the vertical axis VA) which may be independent of the width spanned by the posterior struts 118. The width spanned by the anterior struts 116 may be uniform along their length such that the width at the proximal end 116A is equal to the width at the distal end 116B as shown in FIG. 2C. However, in some embodiments the width spanned by the anterior struts 116 at the proximal end 116A is slightly longer than the width at distal end 116B forming wing-like portions which may facilitate sealing and coaptation. The anterior struts 116 are intended to provide an atraumatic coaptation surface for the anterior leaflet. As such, the anterior struts 116 preferably do not include any cleats 112. Additionally, the width of the anterior struts 116 and/or the spacing between the struts may be adjusted to ensure an atraumatic coaptation structure for the anterior leaflet. In other words, the anterior struts 116 may be wider or more closely spaced than struts 104 and/or struts 118.

The posterior struts 118 may be generally parallel to the vertical axis VA, or they may have a somewhat arcuate shape which conforms with the ventricular wall. In other embodiments, the posterior struts 118 may extend at an angle toward the lumen 102L to reduce contact with the ventricular wall and papillary muscles compared to parallel struts. The posterior struts 118 may extend at an angle alpha (shown in FIG. 3B) ranging between 0 and 70 degrees relative to the vertical axis VA or at an angle beta ranging between 90 and 180 degrees relative to the vertical axis VA to reduce or increase contact with the ventricular wall. By reducing contact between the posterior struts 118 and the ventricular wall, the prosthetic leaflet device 100 may remain in a more constant position with respect to the native annulus. This is expected to provide more consistent coaptation between the prosthetic leaflet device 100 and the opposing native leaflet. Alternatively, providing a concave shape (an angle beta of less than 180 degrees between the atrial and ventricular portions of the posterior wall) may make it easier to position the device appropriately on the annulus and help to prevent device migration in the atrial or ventricular direction.

The posterior struts 118 may include cleats 112 (FIG. 2B) which aid in fixation of the prosthetic leaflet device 100. The cleats 112, for example, abut and engage with the posterior leaflet PL. In some embodiments, the cleats 112 may also engage with the posterior annulus and/or the ventricular wall. The cleats 112 at the ventricular end of the baffle 114 may be shorter to engage the thinner posterior leaflet tissue, whereas the cleats at the annular end of baffle 114 may be longer to engage the annular tissue.

The width W spanned by the posterior struts 118 may be configured to span the full width of the posterior leaflet including all three scallops P1, P2 and P3 (e.g., 25-55 mm). However, according to a presently preferred embodiment, the width spanned by the posterior struts 118 is less than the full width of the posterior leaflet PL. More particularly, the posterior struts 118 are configured to be somewhat wider than the width of the middle scallop P2 (e.g., 20-35 mm) such that the struts 118 displace and at least partially immobilize only the middle scallop P2 or engage only part of scallops P1 and P3. This leaves scallops P1 and P3, or at least a portion of scallops P1 and P3, at least somewhat intact such that they are mobile and able to coapt with the baffle 114 and/or segments A1 and A3 of the anterior leaflet. (See dashed lines of the scallops P1 and P3 in FIG. 2D-2). As a result, if the baffle 114 is slightly wider than the width of middle scallop P2, then the baffle 114 will engage all of scallop P2 and coapt with scallops P1 and P3 even if the prosthetic device 100 is slightly rotationally misaligned with the mitral valve.

In this embodiment, the anterior and posterior struts 116, 118 cooperatively define a basket or pocket 124 (FIG. 2C) having a hollow interior volume and an opening or mouth 126 (FIG. 2C) facing the eyelets 110 (proximal, atrial direction). (See also FIG. 2D-2). Aside from the opening 126, the basket 124 is sealed on all sides by the covering 122. As described above, the fabric covering 108 on the atrial-fixation member 102 is completely optional and moreover may be discontinuous because it is used for tissue ingrowth or protection as opposed to providing a fluid tight seal. In contrast, the fabric covering 122 on the baffle 114 is intended to provide a fluid tight seal with the ventricular wall and the other leaflets of the valve. The shape of the basket 124 is configured to promote the circulation of blood through the hollow interior of the basket 124 and prevent the accumulation of stagnant blood thereby preventing the formation of thrombus. Additionally, the fabric covering 122 is preferably smooth to minimize any trauma to the anterior leaflet as the anterior leaflet coapts against the covering 122.

The covering 122 may be attached to the anterior and posterior struts 116, 118 by any conventional means including sutures, adhesives, sintering or the like. The covering 122 is intended to provide an atraumatic coaptation surface for the anterior leaflet and to prevent leakage of blood in a retrograde direction during systole. The covering 122 may be formed of the same material used for the covering 108 described previously.

The pocket 124 may also be inverted such that the mouth 126 faces downward towards the ventricle (distally), away from the eyelets 110. Still further, the mouth or opening 126 of the basket 124 may be sealed with the covering 122 thereby fully enclosing an interior volume of the pocket 124. This may be advantageous in ensuring non-turbulent blood flow and preventing the formation of thrombus.

The prosthetic leaflet device 100 is implanted in the atrium of the mitral valve such that the baffle 114 is the only portion of the device in contact with the annulus or which crosses the plane of the annulus. (See FIG. 2D). The baffle 114 may incidentally contact the annulus as it extends into the ventricle. In some embodiments, cleats 112 are provided on the posterior struts 118 to engage the annulus, but the prosthetic leaflet device 100 is not otherwise anchored to the annulus. More particularly, in a specific application the lower edge of the atrial-fixation member 102 is implanted 1-10 mm, 1-8 mm, 1-6 mm, 1-4 mm, 3-9 mm, 3-6 mm, 2 mm, 3 mm, 4 mm, 5 mm, 6 mm, 7 mm, 8 mm, or 9 mm above the annulus such that the atrial-fixation member 102 contacts only the wall of the atrium to allow the anterior leaflet to freely open and close under normal physiologic conditions. The atrial-fixation member 102 might be angled such that the anterior segment of the atrial-fixation member 102 is 10-30 mm, 10-20 mm, 10-15 mm, 15-30 mm 15-25 mm, 15-20 mm, 20-30 mm, 10-25 mm, 25-30 mm, 10 mm, 15 mm, 20 mm, 25 mm, or 30 mm above the anterior portion of the annulus or even positioned against the roof of the left atrium. As a result, the baffle 114 is the only portion of the prosthetic device 100 which extends into the left ventricle. (See FIG. 2D).

In several embodiments, the prosthetic leaflet device 100 is retained in place by (a) the atrial-fixation member 102 pressing against the atrial wall and the frictional engagement of the cleats 112 with the atrial wall, and (b) the engagement of the baffle 114 and any cleats 112 on the baffle 114 against the posterior leaflet PL and the annulus. (See, e.g., FIG. 2D-1.) As such, it is advantageous for the atrial-fixation member 102 to bias the cleats 112 into engagement with the atrial wall. For example, the unconstrained size of the atrial-fixation member 102 may be slightly oversized relative to the diastolic size of the atrium, and the atrial-fixation member 102 may be formed of a super-elastic material such as Nitinol® configured to exert a force biasing the cleats 112 into frictional engagement with the atrial wall (away from the lumen 102l). If the atrial-fixation member 102 is formed of a balloon expandable material such as stainless steel, then the atrial-fixation member 102 is expanded to ensure that the cleats 112 engage with the atrial wall during atrial diastole as well as atrial systole.

The atrial-fixation member 102 may have an asymmetric shape with the proximal edge of the anterior portion of the atrial-fixation member 102 vertically displaced relative to the proximal edge of the posterior portion of the atrial-fixation member 102. The height of the anterior portion of the atrial-fixation member 102 may additionally be taller or shorter than the posterior portion of the atrial-fixation member 102.

The stiffness of the atrial-fixation member 102 may be non-uniform with discrete portions of the atrial-fixation member 102 being stiffer than others. For example, the anterior portion of the atrial-fixation member 102 may be more flexible than the posterior portion of the atrial-fixation member 102 or vice versa. There are many ways this may be accomplished. For example, the stiffness of a portion of the atrial-fixation member 102 may be adjusted by the making struts shorter, thicker, or wider, or by reducing the spacing between adjacent struts, such that one portion of the atrial-fixation member 102 is stiffer than another portion.

It may be desirable to modify or otherwise control the shape of the baffle 114 in situ to ensure coaptation and sealing of the anterior leaflet with the baffle. There are a number of ways in which this may be accomplished.

Baffle Including Inflatable Bladder

FIGS. 2E-1 through 2F-3 depict ways to adjust the size and/or shape of the baffle 114 in situ (in the body). FIGS. 2E-1 and 2E-2 show a bladder 115 inserted into the hollow interior 124 of the baffle 114. The bladder 115 may be selectively inflated in situ with saline, blood, gel, or polymer via inflation lumen(s) 117 which extend outside of the body. Inflation of the bladder 115 modifies the shape of the baffle. Notably, inflation of the bladder 115 adjusts the amount the baffle 114 protrudes into the lumen 102L. The anterior struts 116 may be configured to be less rigid than the posterior struts 118 to ensure that the anterior struts 116 preferentially deform inwardly toward axis VA-VA while the posterior struts 118 either do not deform or deform outwardly to a lesser extent than the anterior struts 116 deform inwardly. Inflating the bladder 115 deflects the anterior struts into the lumen 102L and reduces the distance the anterior (opposing) leaflet must travel in order to coapt with the atraumatic surface of the baffle 114. It may be useful for anterior struts 116 to be formed of stainless steel or the like to enable the bladder to plastically (permanently) reshape the anterior struts 116.

FIGS. 2F-1 through 2F-3 show another way to adjust the dimensions of the prosthetic coaptation surface by providing one or more bladders 115 (e.g., identified in FIG. 2F-1 as bladders 115A-C are shown) on the anterior facing portion of the baffle 114. A first bladder 115A may be provided on a central portion of the anterior struts 116, and it can be sized to coincide with the central lobe A1 of the anterior leaflet. Alternatively, the first bladder 115A may be sized to span the full width of the baffle 114 such that bladder coincides with all three lobes A1, A2 and A3. Here, the first bladder 115A serves as the atraumatic coaptation surface. Inflating the bladder modifies the amount the first bladder 115A extends into the lumen 102L thereby reducing the spacing between the baffle and that anterior leaflet.

Figures 1, 2F:
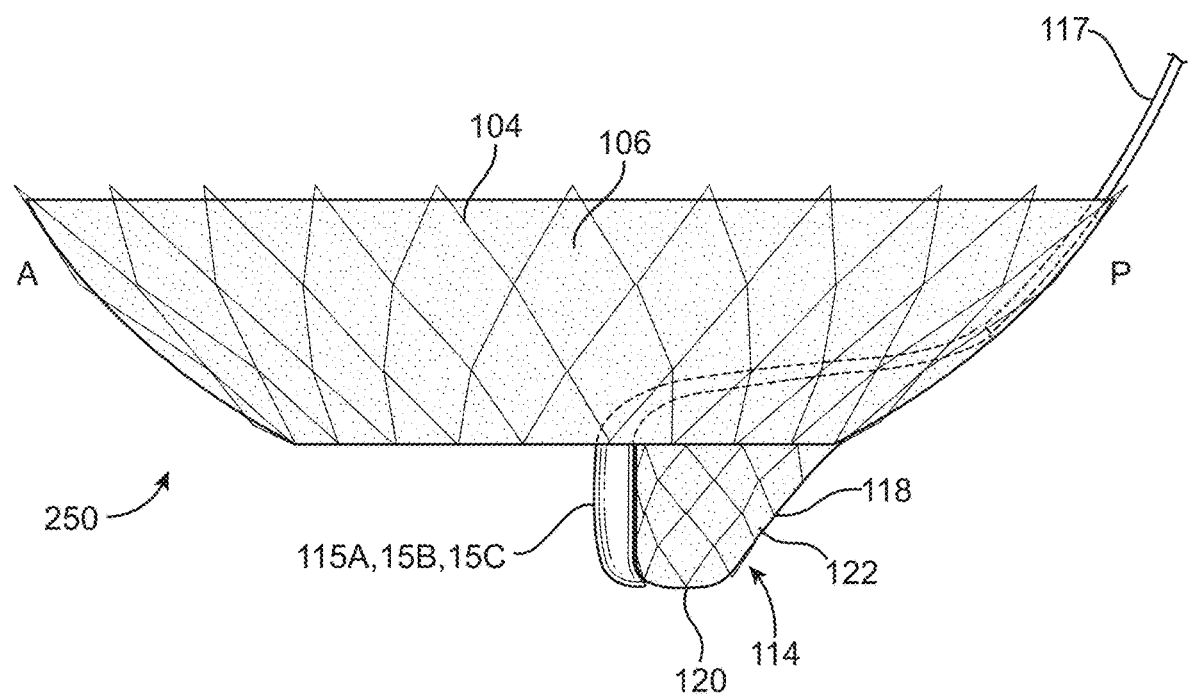
Figures 2, 2F:
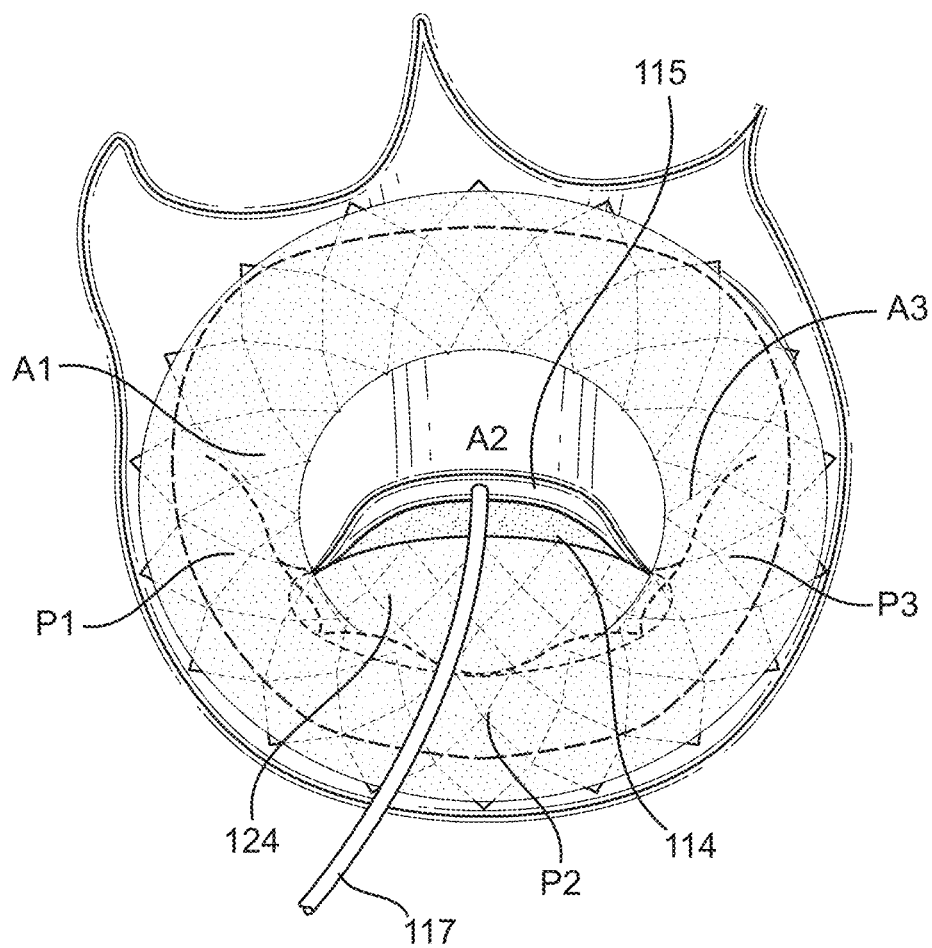
Figures 2, 2F, 3:
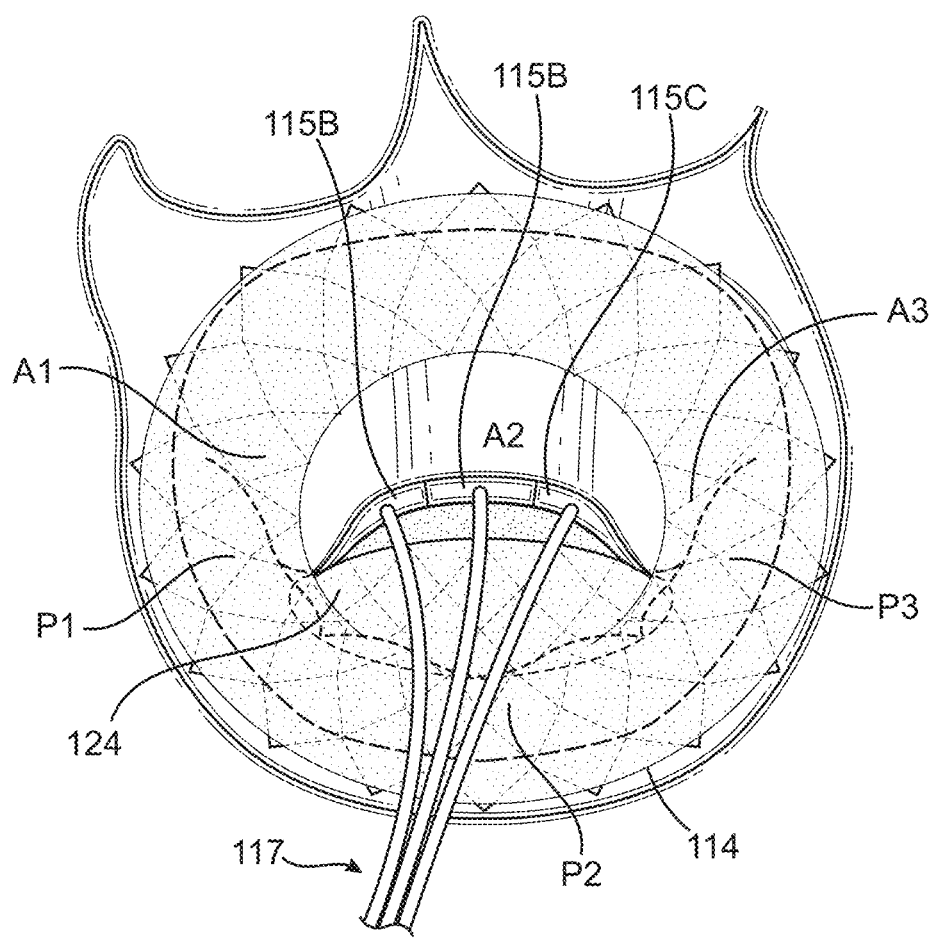
Figures 1, 2G:
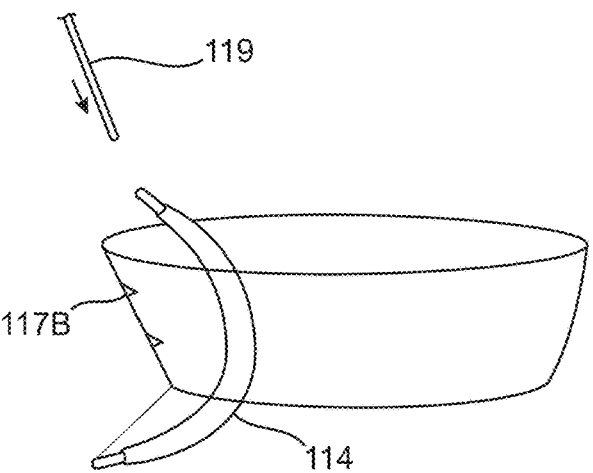
Figures 2, 2G:
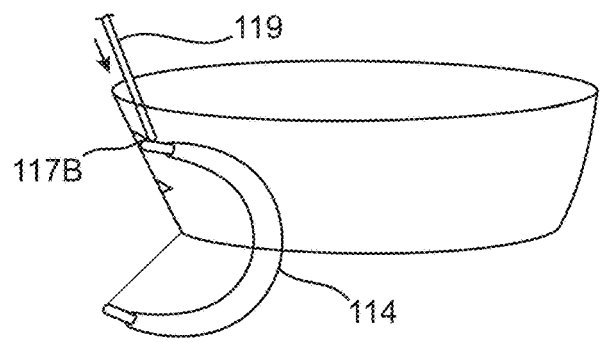
Figures 2, 2G, 3:
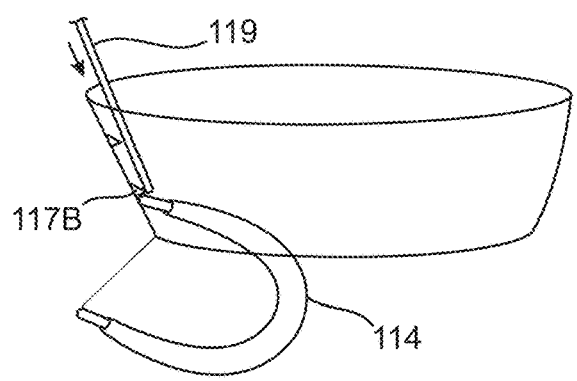
Figures 2, 2G, 3, 4:
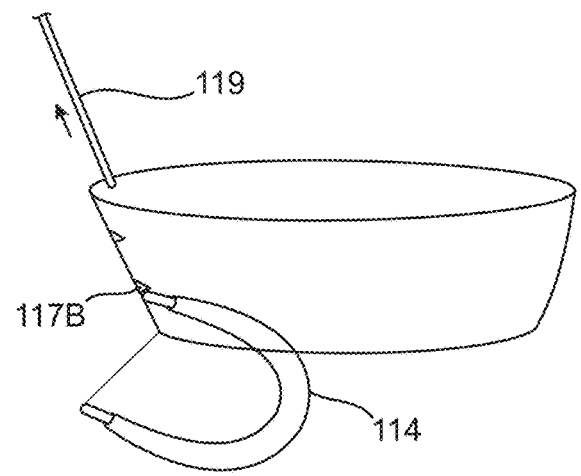

FIG. 2F-3 shows device 250 with bladders 115A, 115B and 115C on the anterior struts 116 configured to coincide with scallops A1, A2 and A3 of the anterior leaflet. Each of the bladders 115A-C can be inflated independently to further control the shape of the baffle 114. As a result, the device 250 can be shaped in-situ to accommodate for rotational displacement of the device 250 with respect to the scallops, A1, A2 and A3 of the anterior leaflet or unique features of a specific anterior leaflet.

Baffle with Adjustment Mechanism

Actuating the shaft 119 adjusts the location of the proximal (atrial) connection between the baffle and the atrial fixation member, which in turn adjusts the amount that the baffle 114 extends into the lumen 102L. Another way to adjust the dimensions and shape of the baffle is to provide one or more adjustment mechanisms 117 such as a worm drive 117A (FIG. 2H) or ratchet 117B (FIGS. 2G-1 to 2G-3) operably connected to the baffle 114 and which are activated by a shaft 119 from outside of the body. FIGS. 2G-1 through 2G-3 show how the shape of the baffle 114 equipped with a ratchet 117B is adjusted by pushing on shaft 119. For example, as the shaft 119 is inserted into the ratchet 117B, the shaft 119 causes the baffle 114 to curve more. As a result, actuating the shaft 119 adjusts the location of the proximal (atrial) connection between the baffle and the atrial fixation member, which in turn adjusts the amount that the baffle 114 extends into the lumen 102L. A suture or cable (not illustrated) is operably connected to the ratchet release to facilitate unlocking the ratchet. The sides of the baffle 114 may be covered with a distensible material 122 such as PTFE or urethane to allow for expansion or contraction of the baffle 114.

Figures 1, 2H:
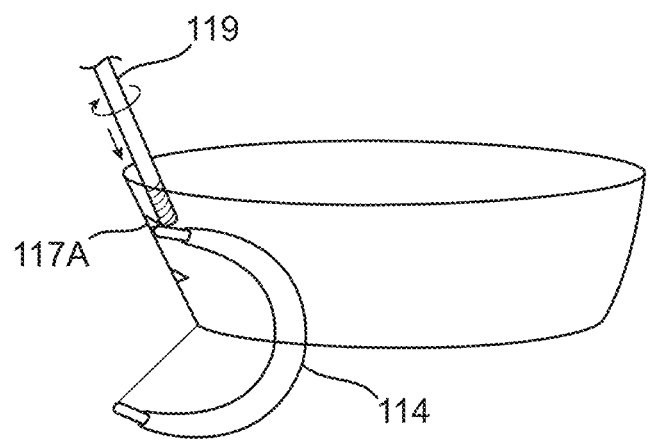
Figures 2, 2H:
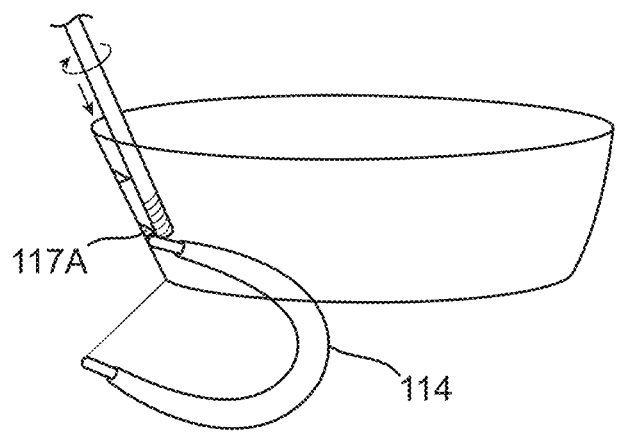

FIG. 2H shows an embodiment of a leaflet prosthetic device having a worm drive 117A adjustment mechanism for changing the shape of the baffle 114. In operation, a shaft 119 with an engagement element at its distal end is engaged with the worm drive 117A. The shaft 119 is rotated causing the worm drive 117A to foreshorten. The foreshortening of the worm drive 117A bends the baffle 114 such that the baffle 114 extends further into the lumen of the prosthetic leaflet device. As a result, the worm drive 117A can adjust the baffle 114 to provide the desired amount of coaptation with the native valve leaflet(s).

Prosthetic Leaflet Device with Skirt or Hem

Figure 2I:
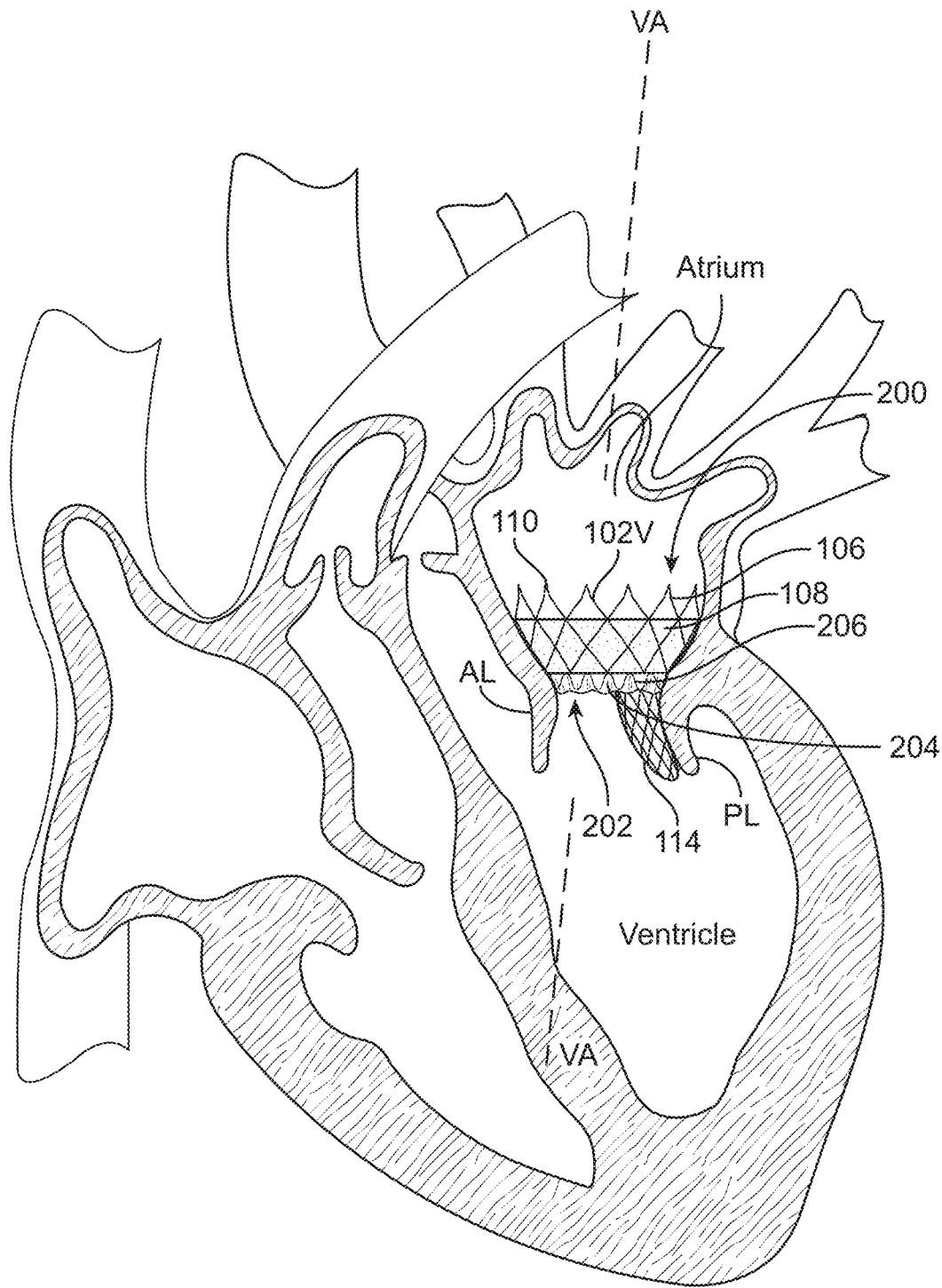

FIG. 2I shows a posterior prosthetic leaflet device 200 which is a slight variation of the posterior prosthetic leaflet device 100 shown above. Similar reference numbers refer to similar features. The prosthetic device 200 has an annular hem 202 which depends or extends in the direction of blood flow (e.g., distally or toward the annulus) from the distal end of the atrial-fixation member. The annular hem 202 includes a covering 204 and a structural reinforcement 206 which biases the covering 204 away from the lumen 102L, i.e., towards the atrial wall. The structural reinforcement 206 may be connected to the prosthetic device 200 by the covering 204 and not otherwise attached to the prosthetic device 200. The covering 204 may be integrally formed with or integrally connected to the covering 108, 122, or the covering 204 may be attached to the atrial-fixation member 102. The covering 204 is configured to promote tissue ingrowth and may be formed of the same or a different material than the covering 108. The structural reinforcement 206 is intended to only provide annular (radial) support to the covering 204 and is specifically configured not to constrain vertical movement of the covering, i.e., movement parallel to the vertical axis VA. More particularly, structural reinforcement 206 biases the covering 204 away from the lumen 102L (into the atrial wall). In use, the prosthetic leaflet device 200 is implanted in the left atrium such that the hem 102 is slightly (0-10 mm) above the mitral valve annulus.

Prosthetic Leaflet Device without Chevrons

FIGS. 3A-3E show a prosthetic leaflet device 250 which is a variation of the posterior prosthetic leaflet device 100. Similar reference numbers refer to similar features. The prosthetic leaflet device 250 does not include the chevrons 102V (FIGS. 2A and 2B) for delivering and positioning the prosthetic device 100. In place of the chevrons 102V and the eyelets 110, prosthetic leaflet device 250 may include a first set of suture loops 252 at least partially spanning the periphery of the baffle 114, and a second set of suture loops 254 at least partially spanning the periphery of the atrial-fixation member 102. The first and second sets of suture loops 252, 254 include two or more suture loops. In the illustrated embodiment, the second set of loops 254 is provided proximate the distal end of the atrial-fixation member 102; however, the loops 254 may be positioned at any location on the atrial-fixation member 102 as desired. A third set of loops may be provided on the atrial-fixation member 102 if desired and may be cinched independently of suture loops 252 and 254. The suture loops 252, 254 are configured to receive a filament (suture) 2525, 2545 or the like which may be used to selectively collapse the atrial-fixation member 102 and/or the baffle 114 by tightening the suture. The baffle 114 and atrial-fixation member 102 may be collapsed independently of one another. Collapsing the atrial-fixation member 102 and the baffle 114 facilitates repositioning and/or re-sheathing and removal of the prosthetic leaflet device 250.

One or more additional suture loops 256 may be provided on the baffle 114 and is/are configured to receive a filament (suture) 2565. Suture loop(s) 256 are optional and may be used to compress the baffle 114 for repositioning or removal. Suture loops 256 may also be used to evert the prosthetic leaflet device 250 by pulling on suture 2565 as an alternative method to disengage the prosthetic leaflet device 250 from the annulus for repositioning and/or re-sheathing of the prosthetic device 250. In the illustrated embodiment the third suture loop(s) 256 are provided on the anterior side of the baffle 114, i.e., the side facing the lumen 102L.

Figure 3A:
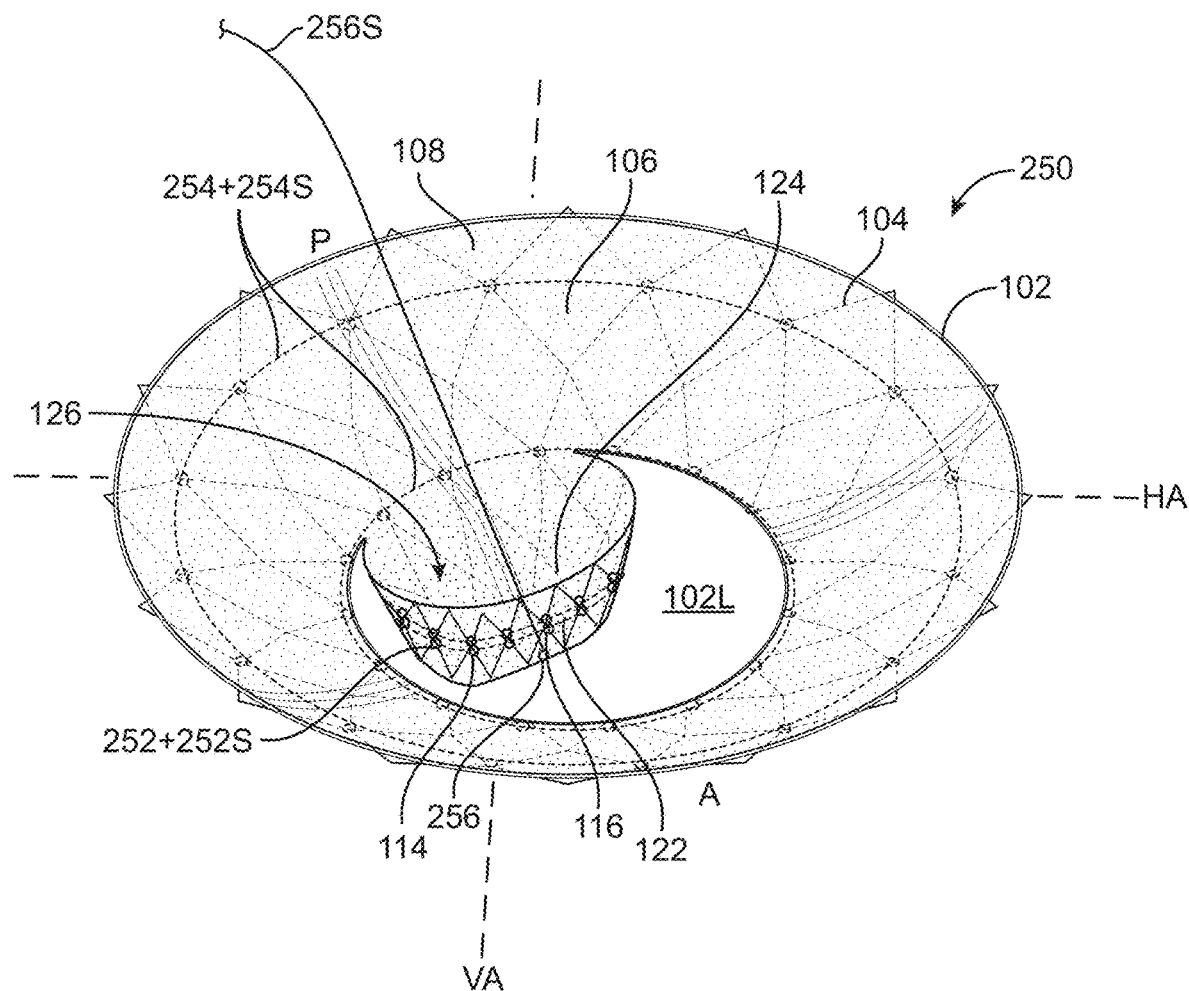
FIGS. 3A-3E are views of a prosthetic leaflet device in accordance with embodiments of the present technology.
Figure 3B:
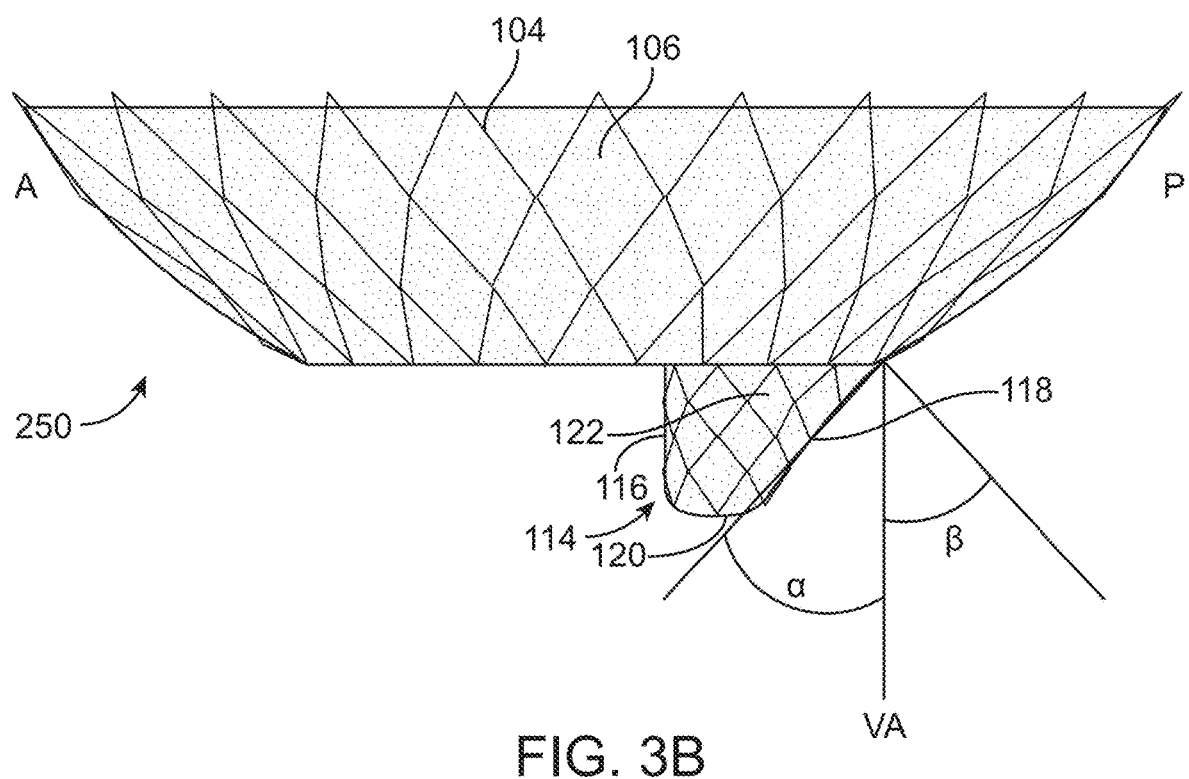
Figure 3C:
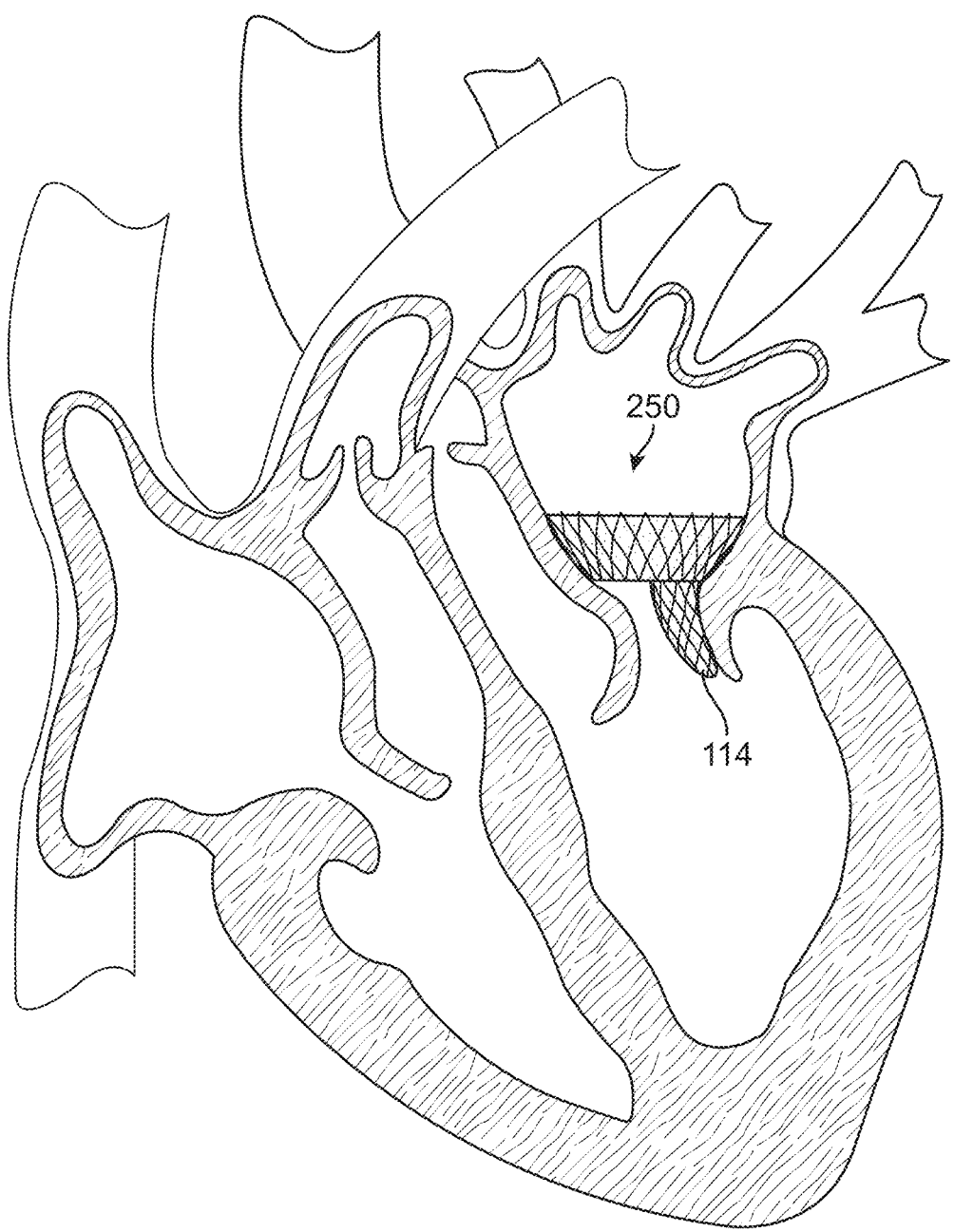
Figure 3D:
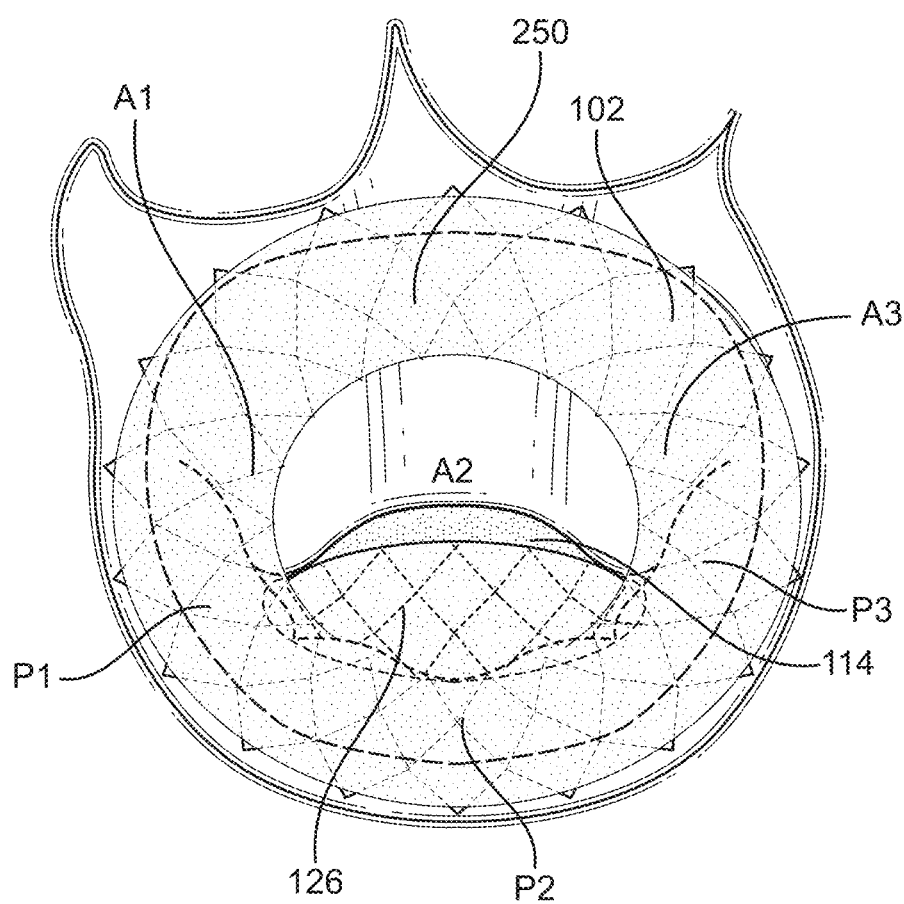
Figure 3E:
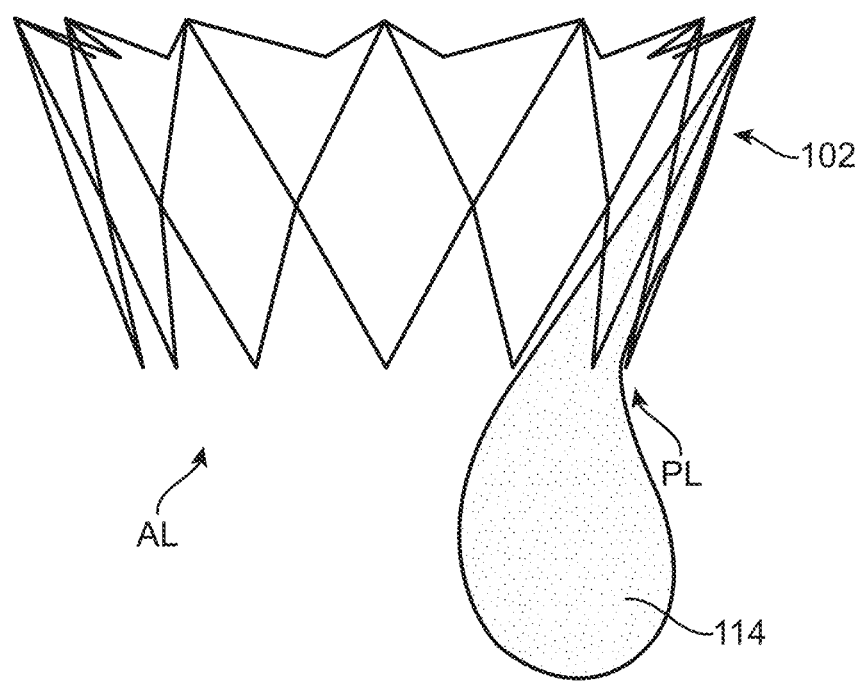

As best seen in FIG. 3B, the posterior struts 118 of the baffle 114 may extend at an angle alpha relative to the vertical axis. In other words, the baffle 114 may be angled inwardly away from the ventricular wall towards the lumen 102l in the direction of blood flow. This configuration spaces the downstream end of the baffle 114 radially inward of the ventricular wall or at least reduces the force exerted by the ventricular wall against the baffle 114 compared to some embodiments of the baffle 114 described above with respect to FIGS. 2A-2E. This is expected to reduce movement of the prosthetic device 250.

Alternatively, the posterior side of the baffle 114 may include a small notch or other indentation (not illustrated) extending laterally at an elevation corresponding to the position of the native annulus on the baffle 114 to provide additional clearance for the annulus. Alternatively, the posterior side of the baffle 114 may be angled outwardly toward the ventricular wall (away from the lumen 102l) to enhance the radial outward force exerted against the native annulus to aid in anchoring in the posterior sub-annular space.

In some embodiments, the baffle 114 is formed of a biocompatible foam. This foam may be compressible to enable delivery through a small catheter and be self-expanding to resume its desired shape after delivery. A portion or all of the foam baffle 114 may be further covered by a biocompatible material such as expanded polytetrafluoroethylene to enhance tissue ingrowth or atraumaticity of the coaptation surfaces. The baffle 114 may, for example, have a teardrop shape. (See, e.g., FIG. 3E.) The foam baffle 114 may include struts, e.g., on a posterior portion thereof which are connected to a posterior portion of the atrial-fixation member. The posterior portion of the baffle 114 may include frictional elements such as cleats 112 configured to engage with the posterior leaflet and possibly the annulus.

Prosthetic Leaflet Device with Partial Anterior Atrial-Fixation Member

Figure 4A:
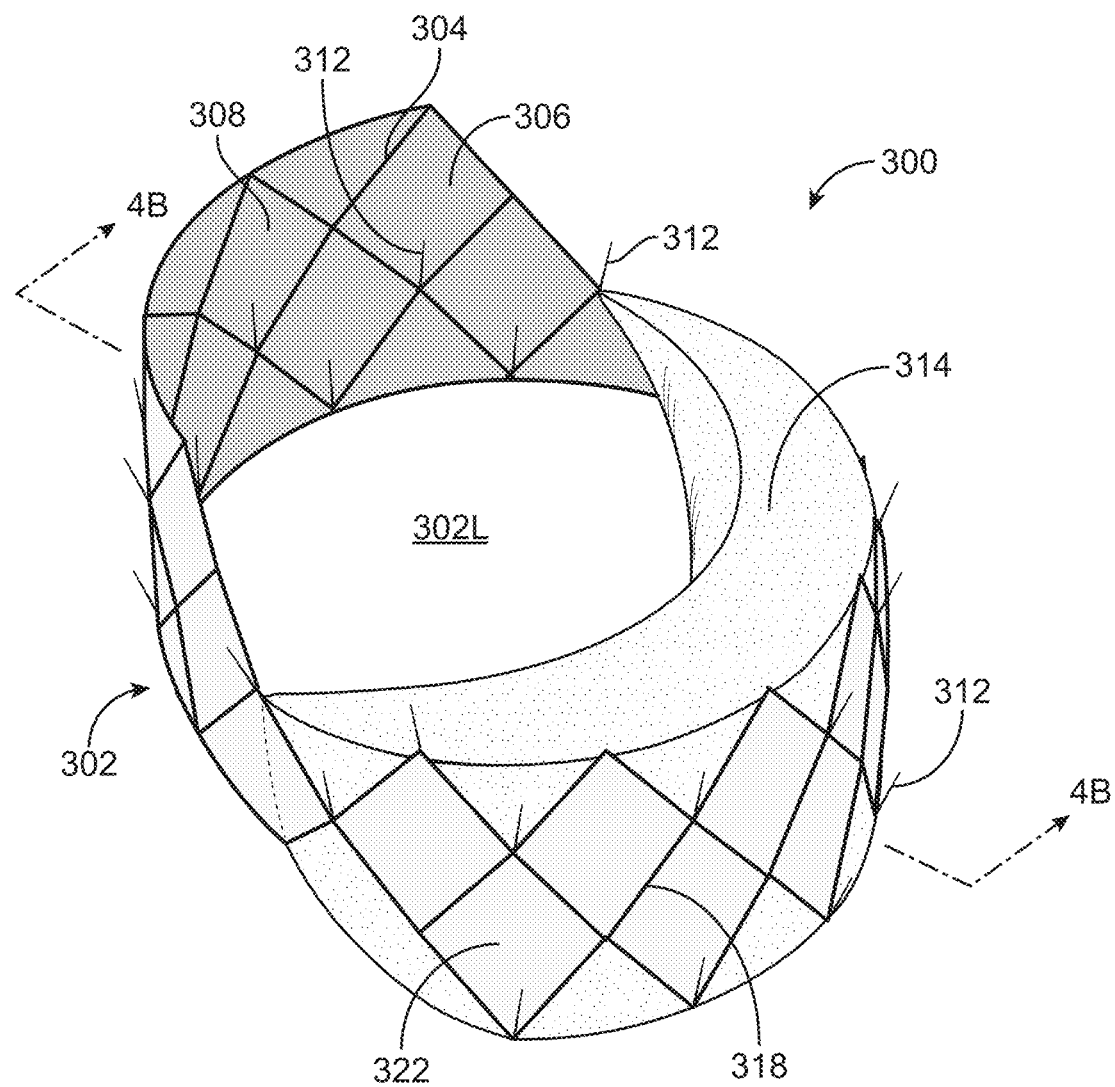
FIGS. 4A-4B are views of a prosthetic leaflet device in accordance with embodiments of the present technology.
Figure 4B:
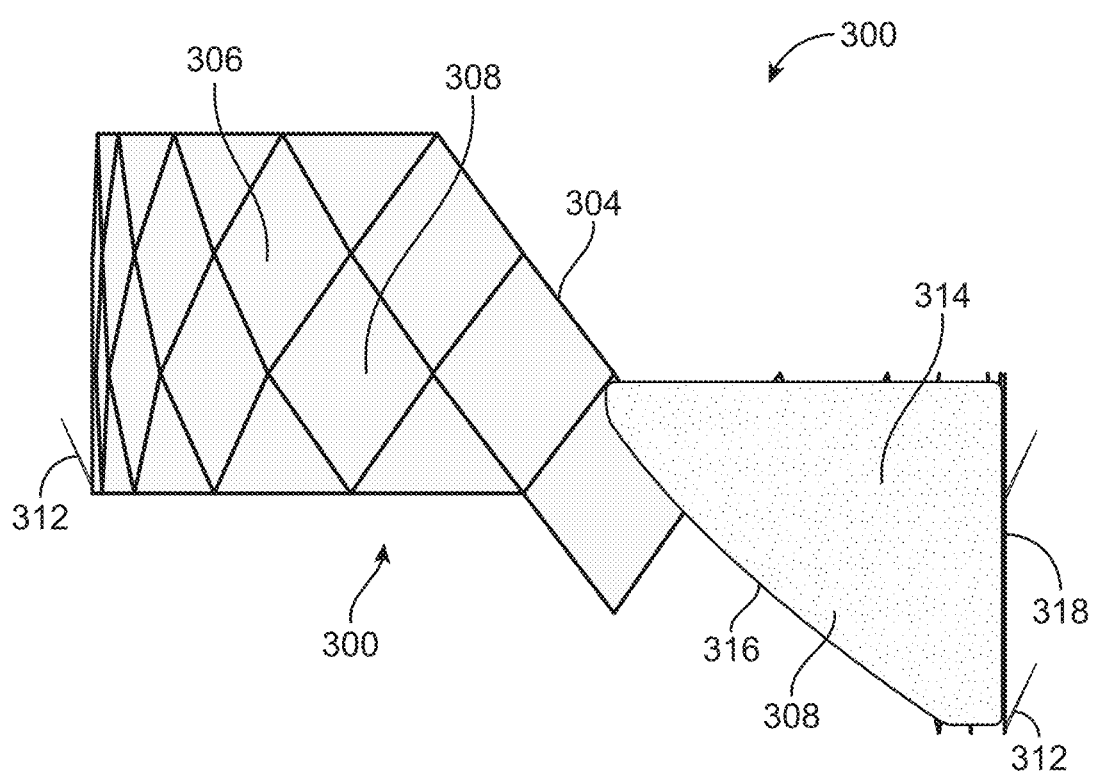

FIGS. 4A and 4B show a prosthetic leaflet device 300 having an atrial fixation member 302 configured to span part or all of the perimeter of the anterior leaflet (e.g., scallops A1, A2 and A3). The atrial fixation member 302 can include struts 304 in a diamond pattern or another suitable pattern. Each cell of the atrial-fixation member 302 defines an opening or through hole 306. The unconstrained shape of the atrial-fixation member 302 may be generally circular or oval shaped. The atrial-fixation member 302 can have any number of through holes 106 or any shape or size such that the atrial-fixation member 302 contacts the left atrial wall with at least a threshold amount of radial force to fix the position of the prosthetic leaflet device 300. The radial force may be adjusted by varying the shape and dimensions of the struts (e.g., the thickness, width, and spacing between struts) and the shape and dimensions of the through holes 306.

The atrial-fixation member 302 may be formed of any biocompatible material such as stainless steel, a nickel-titanium alloy or a polymer. The atrial-fixation member 302 could be an elastic self-expanding material or a balloon-expandable material. According to a presently preferred embodiment, the atrial-fixation member 302 is formed of a super-elastic nickel-titanium alloy, e.g. Nitinol®, that is self-expanding.

The prosthetic leaflet device 300 further includes a baffle 314 attached to or integral with the atrial fixation member 302. The atrial fixation member 302 and baffle 314 cooperatively define a lumen 302L through which blood flows. The baffle 314 is configured to protrude into the lumen 302L to provide an atraumatic coaptation surface for the anterior leaflet. In use, the prosthetic device 300 is implanted with the atrial fixation member 302 in the atrium and the baffle 314 extending from the atrium, across the annulus, and into the ventricle. All or part of the posterior leaflet is/are pushed out of the way by the baffle 314. Several embodiments of the prosthetic device 300 are sized to coincide with the central lobe P2 of the posterior leaflet without contacting at least a portion of the lobes P1 and P3, such that lobes P1 and P3 remain mobile and can coapt with the baffle 314. This may allow the baffle 314 to be smaller than the baffle 114 described above, which in turn is expected to reduce the forces exerted on the baffle 314 for enhancing long-term fixation of the prosthetic device 300.

The atrial fixation member 302 and/or the baffle 314 may optionally include frictional elements such as cleats 312 adapted to frictionally engage (non-invasively) with the annulus, atrial wall, and/or posterior leaflet without penetrating (piercing) into the tissue. If desired, the cleats 312 may have sharpened ends configured to pierce into the tissue. In some embodiments, the cleats 312 are on the anterior portion of the atrial fixation member 302 and on the posterior portion of the baffle 314. In a particular embodiment, the cleats 312 are not on the lateral sides of either the atrial fixation member 302 or the baffle 314. The cleats 312 may engage the anterior atrial wall, posterior leaflet and/or the posterior annulus. The prosthetic leaflet device 300 may include additional anchoring elements such as hooks, barbs, screws, etc.

In some embodiments, the baffle 314 is formed of a biocompatible foam. The posterior portion of the baffle 314 may include frictional elements such as cleats 312 configured to engage with the posterior leaflet and possibly the annulus.

In other embodiments, the baffle 314 may be an open or closed basket-shaped baffle such as the one shown in FIG. 2B. The baffle 314, for example, may be similar to the baffle 114 described above in FIGS. 2B and 2C such that the anterior struts 316 and posterior struts 318 (FIG. 4B) define a portion of the baffle 314 and can be covered by a biocompatible covering 322 which may be the same material used for covering 108 described previously. The baffle 314 is configured to provide an atraumatic coaptation surface for the anterior leaflet in mitral applications. As described previously, the spacing, between struts 316 and the width of the struts 316 may be varied to ensure an atraumatic coaptation surface for the anterior leaflet.

Trigonal Anchor and/or Posterior Hook

Figure 5A:
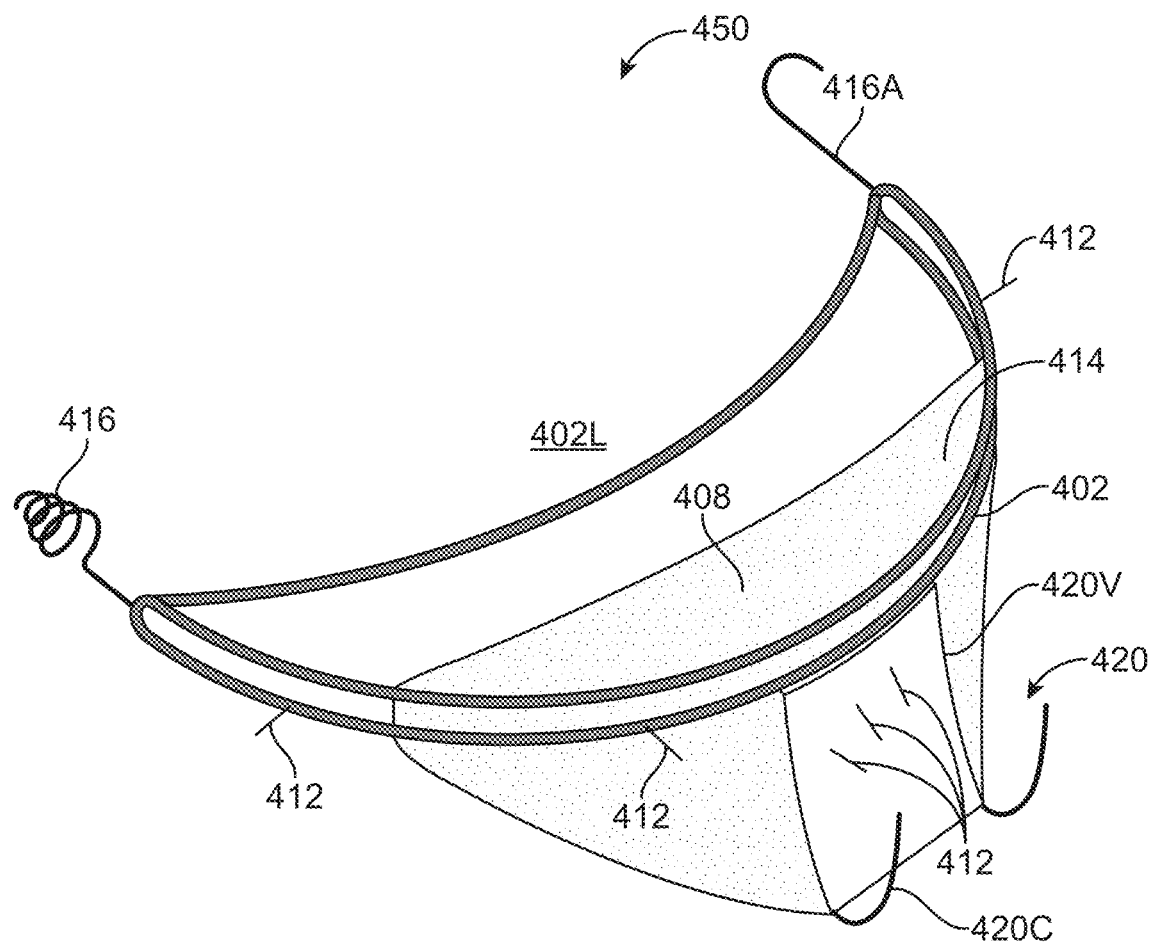
FIGS. 5A-5B are views of a prosthetic leaflet device in accordance with embodiments of the present technology.
Figure 5B:
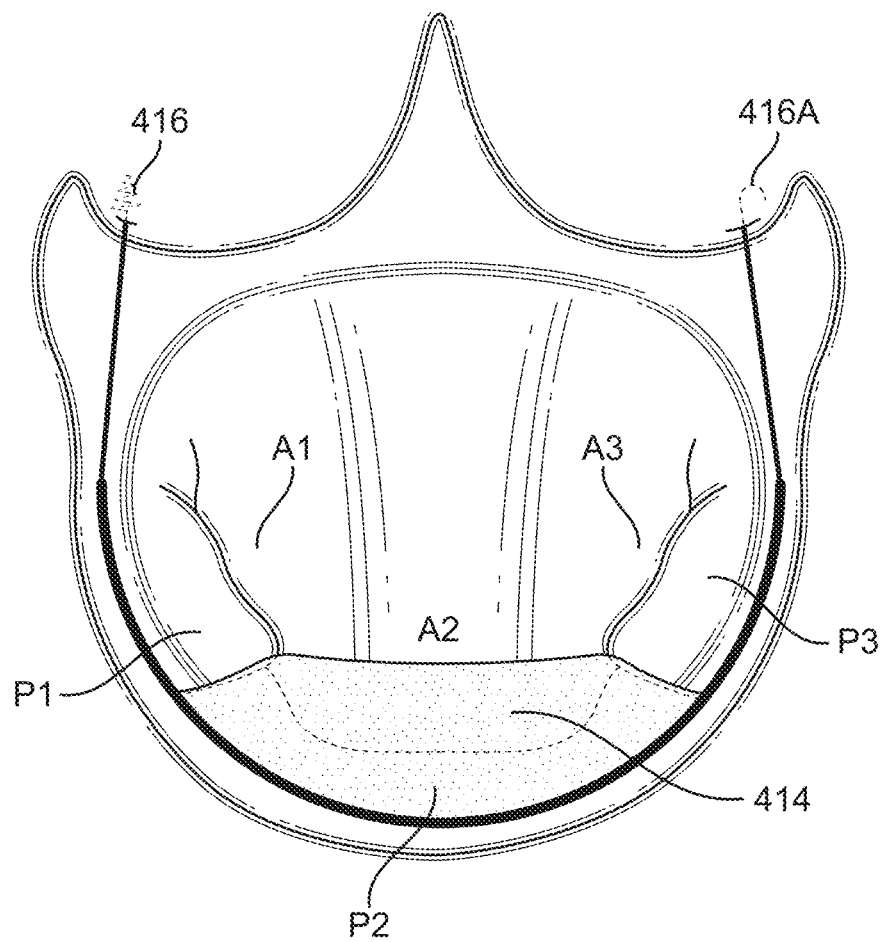

FIGS. 5A-5B Illustrate another prosthetic leaflet device 450 which is a variation of the prosthetic device 300. The prosthetic device 450 includes a fixation ring 402 (e.g., a partially circular ring, a partially oval ring, etc.) configured to span the perimeter of part or all of the posterior leaflet (scallops P1, P2 and P3), i.e., up to the leaflet commissures. The prosthetic leaflet device 350 replaces the atrial-fixation member 302 of prosthetic device 300 with one or more trigonal extensions 416, 416A. The trigonal extensions 416, 416A extend to the fibrous trigones (FIG. 1). To avoid impinging on the anterior leaflet, the trigonal extension may be offset vertically (proximally—toward the atrium and away from the annulus) and/or may be curved so as to skirt the perimeter of the annulus. The prosthetic device 450 may optionally include cleats 412 on the baffle and/or on the ring 402. FIG. 5A depicts the prosthetic device 350 with both trigonal extensions and posterior hooks, but the illustrated embodiment is not intended to be limiting, such that each of these features could be separately incorporated into the prosthetic device 450 either in addition to or instead of the anterior atrial-fixation member and the posterior cleats. The trigonal extensions 416, 416A are adapted to engage the fibrous trigones. The trigonal extension 416 has an anchor at the distal end of the extension configured to pierce into the fibrous trigone, whereas the trigonal extension 416A has an atraumatic (curved or blunt) end adapted to non-invasively engage with the fibrous trigone. For the sake of illustration, the prosthetic leaflet device shown in FIG. 5A has one each of the trigonal extensions 416 and 416A, but in use the prosthetic leaflet device would normally include one set of common trigonal extensions 416 or one set of common trigonal extensions 416A.

The trigonal extensions 416, 416A may extend (parallel to the horizontal axis HA) from the ring 402 to the fibrous trigone. The trigonal extensions 416, 416A may be straight or curved. To minimize disruption to the normal movement of the anterior leaflet, it may be desirable for the trigonal extensions 416, 416A to have an arcuate shape to skirt the perimeter of the anterior annulus. Additionally, or alternatively, the trigonal extensions may extend somewhat vertically (proximally) from the ring 402 to avoid the anterior leaflet.

The prosthetic leaflet device 450 may optionally include one or more posterior hooks 420 attached to a posterior portion of the ring 402. Although not separately illustrated, the posterior hook 420 may be provided in place of, or in addition to, the posterior cleats 412 which engage the posterior leaflet and/or the posterior annulus. The posterior hook 420 includes a generally straight portion 420V extending distally in a generally vertical direction and a portion 420C which curves in a posterior direction configured to atraumatically engage the ventricular side of the annulus, the posterior ventricular wall, and/or the edge of the posterior leaflet.

The prosthetic leaflet device 450 includes a baffle 414 attached to the distal partial ring 402 that protrudes into lumen 402L and which provides an atraumatic coaptation surface for the anterior leaflet. In mitral valve applications, the prosthetic device 350 is implanted with the trigonal extensions 416, 416A at the level of the annulus such that the baffle 414 extends into the ventricle. The baffle 414 displaces all or part of the posterior leaflet out of the way. According to several embodiments, the prosthetic device 350 is sized to coincide with the central lobe P2 of the posterior leaflet, such that lobes P1 and P3 are mobile and able to coapt with the baffle 414. See FIG. 6B.

In some embodiments, the baffle 414 is formed of a biocompatible foam. The baffle 414 may, for example, have a teardrop shape. In other embodiments, the baffle 414 has a basket shape enclosing a hollow interior volume as shown and described with reference to FIG. 2B. Thus, the basket-shaped baffle 414 may include a plurality of struts covered by a biocompatible covering 408 which may be the same material used for covering 108 described previously. The baffle 414 is configured to block regurgitant blood flow and to provide an atraumatic coaptation surface for the anterior leaflet.

Prosthetic Leaflet Device with Posterior Atrial-Fixation Member

Figure 6A:
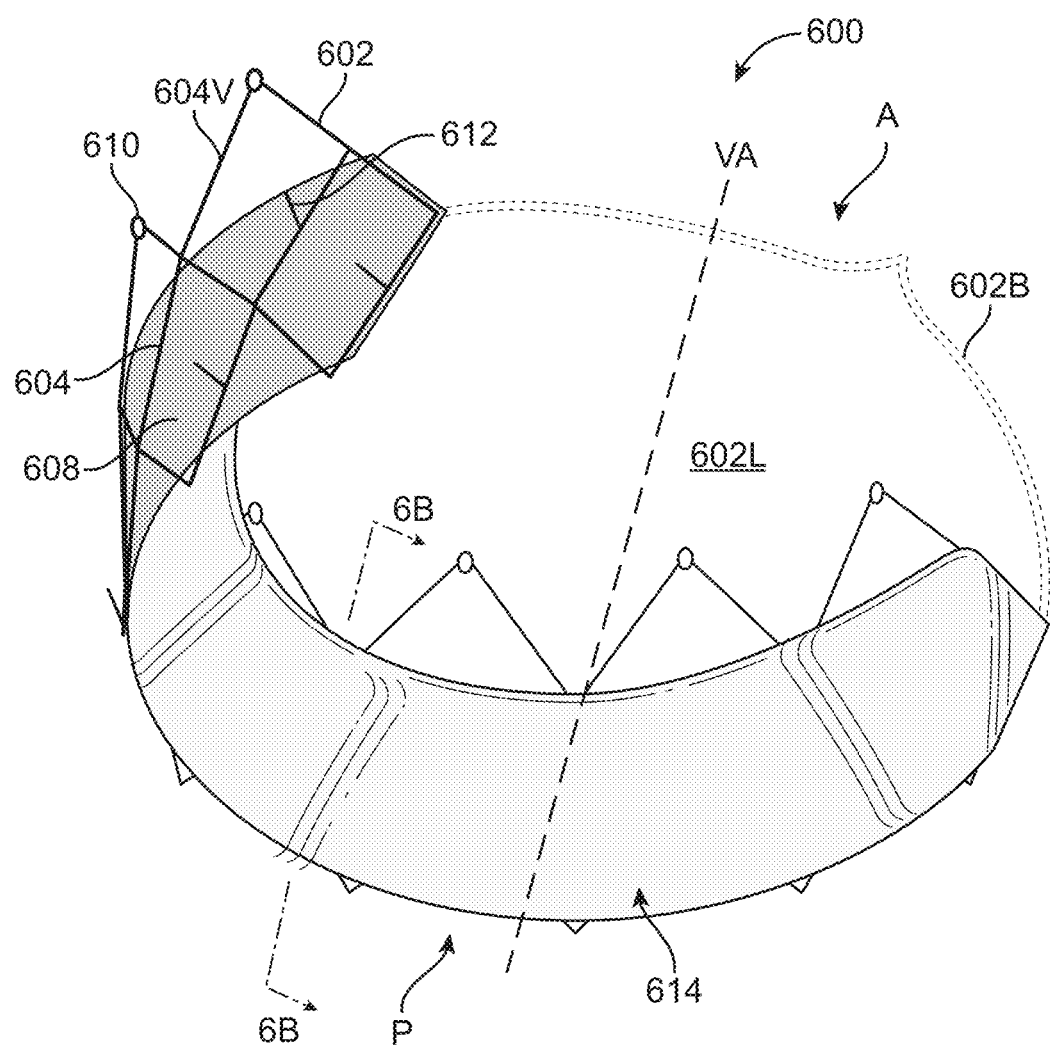
FIGS. 6A-6B are views of a prosthetic leaflet device in accordance with embodiments of the present technology.
Figure 6B:
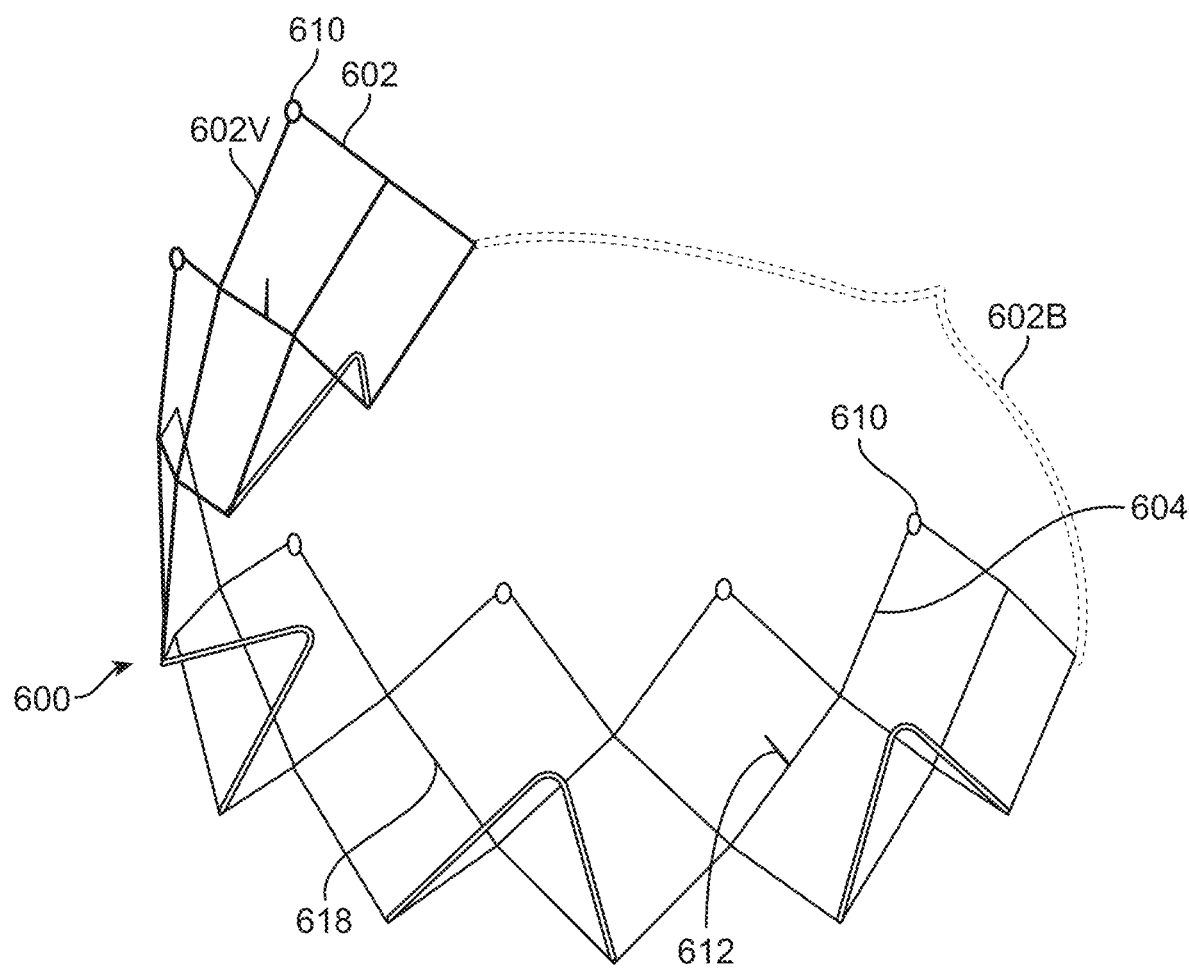

FIGS. 6A-6B show a prosthetic leaflet device 600 including a fixation ring member 602 formed of a mesh, such as a braid or stent-like structure, having wires or struts 604 defining a plurality of cells where each cell has a through hole or opening 606. For clarity, the prosthetic leaflet device 600 is shown inverted for a mitral valve application such downstream end is above the upstream end. The size, shape and number of the openings 606 are selected to optimize the radial force to ensure fixation. An optional bridging element 602B (shown in phantom) may connect the ends of the fixation ring member 602 together such that the bridging element 602B and the fixation ring member 602 cooperatively define a lumen 602L which in operation fluidically couples the atrium and the ventricle. The ring segment 602 and the bridging element 602B may be formed of any biocompatible material, including a super-elastic self-expanding material such a nickel-titanium alloy or a balloon-expandable material such as stainless steel. For example, the ring segment 602 and the bridging element 602B are formed of a nickel-titanium alloy.

The prosthetic device 600 has a vertical axis VA in the direction of blood flow from the atrium to the ventricle and a horizontal axis orthogonal to the vertical axis. The prosthetic leaflet device 600 has an anterior side and a posterior side.

The ring segment 602 includes a plurality of baffle supports (struts) 613 (FIG. 6B) attached to or integrally formed with the ring 602. The prosthetic device 600 further includes a baffle 614 attached to struts 613.

In some embodiments, the baffle 614 is formed of a biocompatible foam. The baffle 614 may, for example, have a teardrop shape. The posterior portion of the baffle 614 and/or the struts 613 may include a plurality of frictional engagement portions or cleats 612 configured to engage with the posterior leaflet and possibly the annulus.

In other embodiments, the baffle 614 may have a basket shape (such as the baffle 114 shown in FIG. 3A) with a biocompatible covering 608 attached to the struts 618 to form a convex atraumatic surface against which the anterior leaflet may coapt. The baffle 614 protrudes into lumen 602L such that a portion of the baffle 614 approximates the closed position of the posterior leaflet. The smoothness of the baffle, width of the struts 618, and spacing between the struts 618 all contribute to providing an atraumatic coaptation surface.

The biocompatible covering 608 may be a fabric formed of a polymer or biomaterial (Polyethylene terephthalate (PET), expanded polytetrafluoroethylene (ePTFE), silicone, urethane, pericardium, etc.). The covering 608 may be attached to the ring segment 602 by any conventional means including sutures, adhesives, sintering or the like. In some embodiments the covering 608 is sutured to the struts 618.

The uppermost row of struts 604 of the fixation ring 602 located at the most upstream end of the prosthetic device 600 form a plurality of inverted V-shaped structures or crown points or chevrons 604V. Some, but not necessarily all, of the chevrons 604V include an eyelet 610 at the apex of the V. The eyelets 610 are sized to receive suture strands (not illustrated) used to deliver, orient and retrieve the prosthetic leaflet device 600 to/from the delivery catheter (not illustrated). The chevrons 604V may extend generally vertically (parallel to the vertical axis VA) or they may be angled toward the lumen 602L.

The fixation ring 602 and the bridging portion 602B may include a plurality of frictional engagement elements or cleats 612 which are adapted to frictionally engage the walls of the atrium. In some embodiments, the cleats 612 may have a sharpened end configured to pierce into the tissue of the atrial wall. The fixation ring 602 is configured to straddle the posterior mitral valve annulus with part of the ring in the atrium and part in the ventricle. The bridging portion 602B is configured to skirt the perimeter of the anterior annulus or possibly extend from the anterior commissure to the posterior commissure to avoid interfering with the anterior leaflet and does not extend into the ventricle. The cleats 612 may be integrally formed with or integrally attached to the struts 604 and may extend upstream toward the eyelets 610 (e.g., proximally, away from the ventricle in mitral valve applications in mitral valve applications) and/or downstream away from the eyelets 610 (e.g., distally, toward the ventricle), or they may face in both directions. The cleats 612 are integrally formed with the struts and extend proximally toward the eyelets 610.

Prosthetic Leaflet Device with Posterior Hook

Figure 7A:
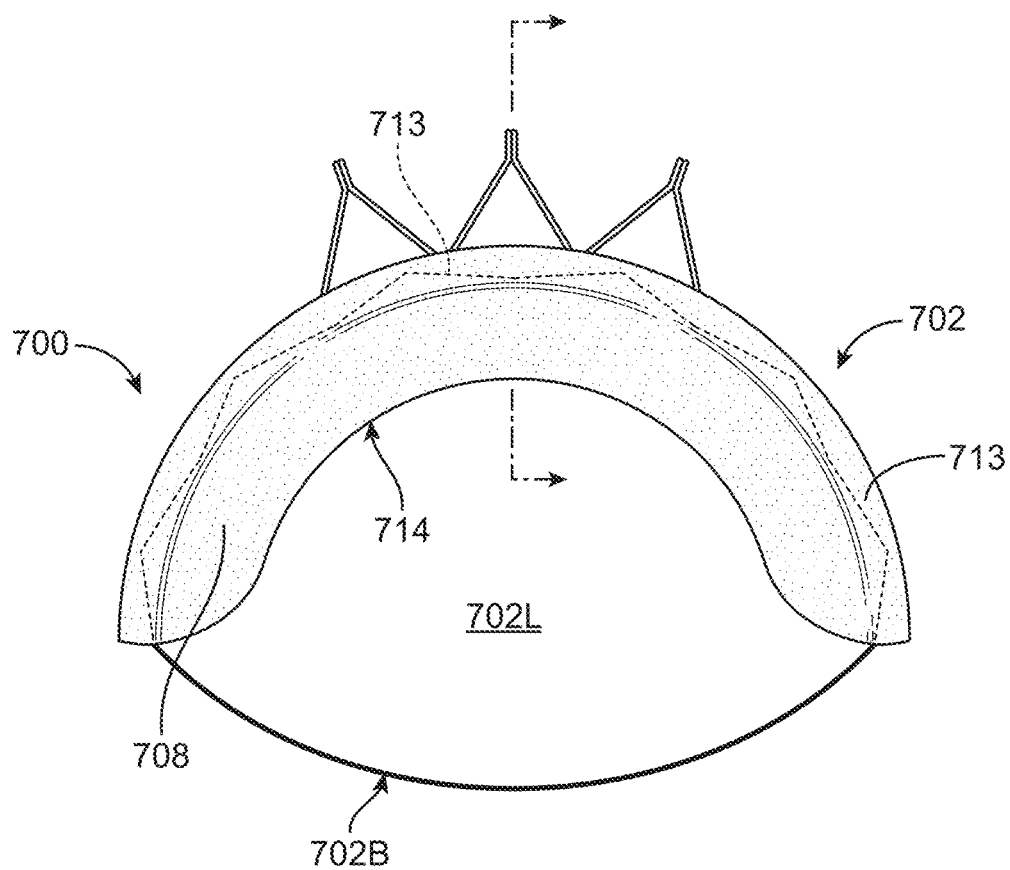
FIGS. 7A-7C are views of a prosthetic leaflet device in accordance with embodiments of the present technology.
Figure 7B:
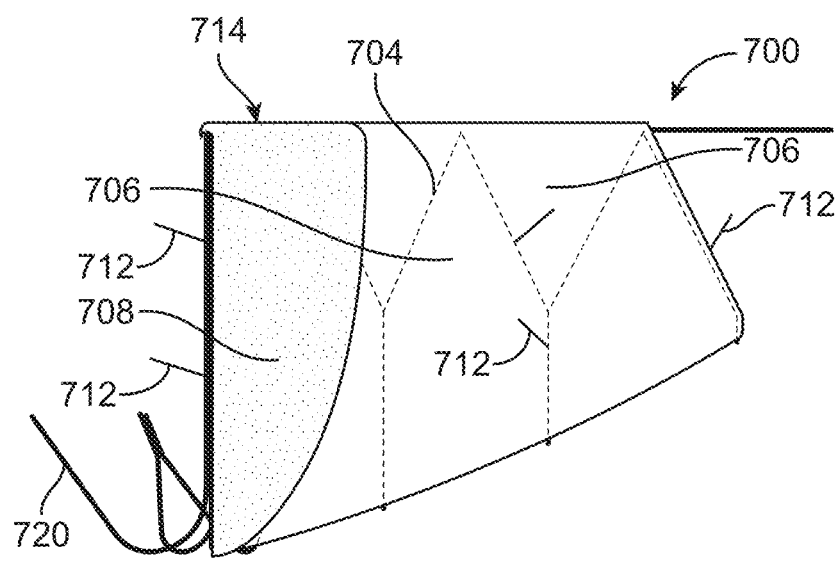
Figure 7C:
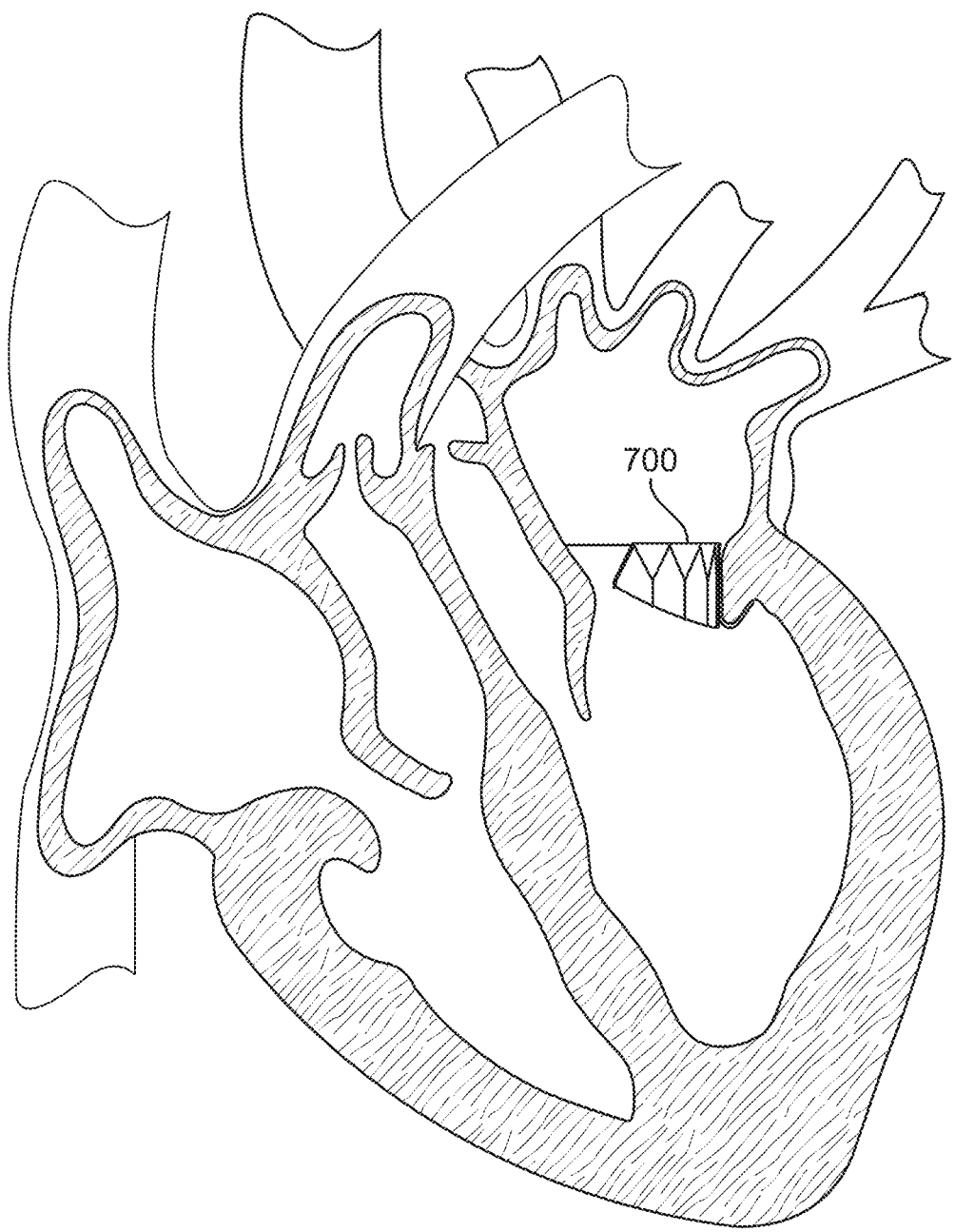

FIGS. 7A-7C depict a prosthetic leaflet device 700 including a fixation ring segment 702 formed of a mesh or stent-like material having a plurality of struts 704 defining a plurality of cells where each cell has a through-hole or opening 706. The size, shape and number of the openings 706 can be configured to provide sufficient fixation of the prosthetic device 700 without exerting too much force against the tissue. The prosthetic device 700 can further include a bridging element 702B that connects the ends of the ring segment 702 together such that the bridging element 702B and the ring segment 702 cooperatively define a lumen 702L which in operation fluidically couples the atrium and the ventricle. The ring segment 702 and the bridging element 702B may be formed of any biocompatible material, including a super-elastic self-expanding material such a nickel-titanium alloy or a balloon-expandable material such as stainless steel. For example, the ring segment 702 and the bridging element 702B are formed of a nickel-titanium alloy in a specific embodiment. The ring segment 702 includes a plurality of baffle supports (struts) 713 attached to or integrally formed with the ring segment 702.

The prosthetic device 700 further includes a baffle 714 attached to the struts 713. In some embodiments, the baffle 714 is formed of a biocompatible foam. The baffle 714 may, for example, have a teardrop shape. The posterior portion of the baffle 714 may include a plurality of frictional engagement portions or cleats 712 configured to engage with the posterior leaflet and possibly the annulus. In other embodiments, the baffle may have a basket shape (such as baffle 114 in FIG. 3A) with a biocompatible covering 708 attached to the supports 713 to form baffle 714 which provides an atraumatic surface against which the anterior leaflet may coapt. The biocompatible covering 708 may be a fabric formed of a polymer or biomaterial (Polyethylene terephthalate (PET), expanded polytetrafluoroethylene (ePTFE), silicone, urethane, pericardium, etc.). The covering 708 may be attached to the ring 702 by any conventional means including sutures, adhesives, sintering or the like. Thus, in use the baffle 714 replaces the posterior leaflet.

The ring segment 702 and the bridging portion 702B may include a plurality of frictional engagement portions or cleats 712 which are adapted to frictionally engage the walls of the atrium. For example, the cleats 712 can "tent" into the tissue without piercing into the tissue of the atrial wall. The ring segment 702 is configured to straddle the posterior mitral valve annulus with part of the ring in the atrium and part in the ventricle. The bridging portion 702B is configured to skirt the perimeter of the anterior annulus and does not extend into the ventricle. The cleats 712 may be integrally formed with or integrally attached to the struts 704, and they may extend upstream (e.g., proximally, away from the ventricle) and/or downstream (e.g., distally, toward the ventricle), or they may face in both directions. In the illustrated embodiment, the cleats 712 are integrally formed with the struts and extend proximally (upward).

The prosthetic leaflet device 700 may optionally include a posterior hook 720 attached to a posterior portion of the ring segment 702. The posterior hook 720 is configured to atraumatically engage the ventricular side of the annulus, the posterior ventricular wall, and/or free edge of the posterior leaflet. (See, FIG. 7C.). This is expected to further fix the prosthetic leaflet device 700 in place while also retaining the native posterior leaflet.

Semi-Circular Prosthetic Leaflet Device

Figure 8A:
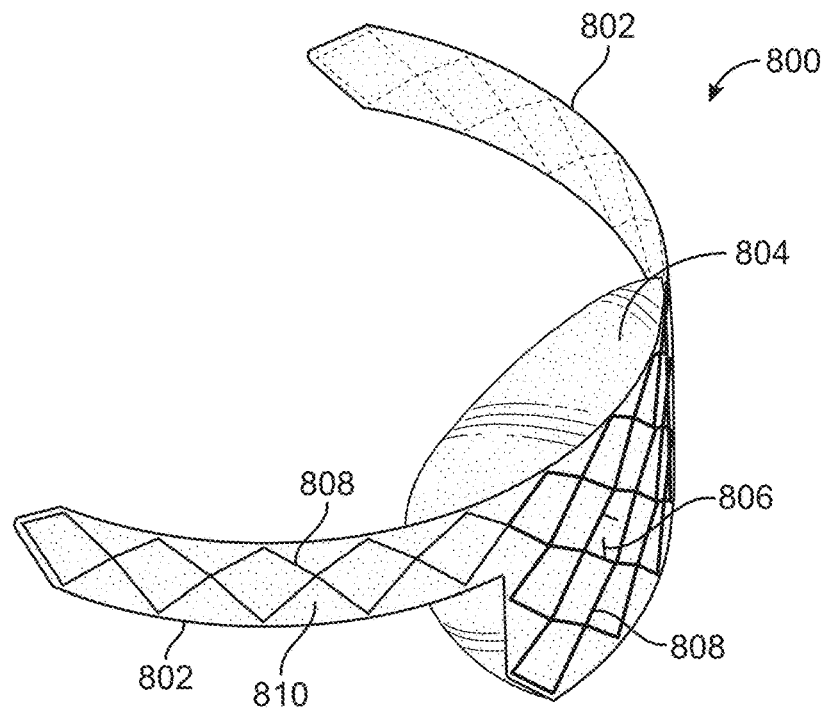
FIGS. 8A-8B are views of a prosthetic leaflet device in accordance with embodiments of the present technology.
Figure 8B:
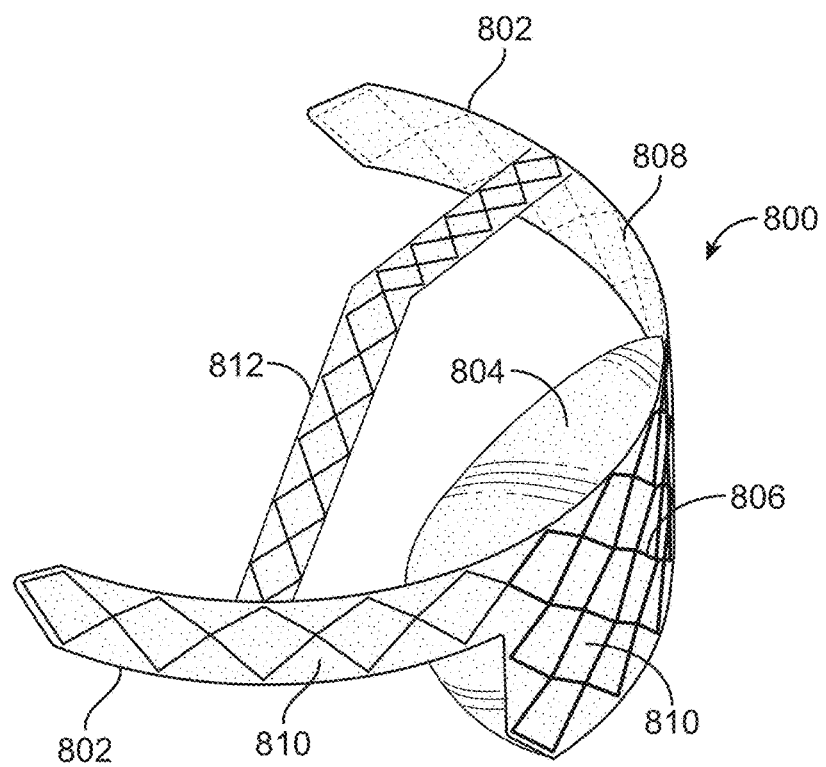

FIGS. 8A and 8B show a prosthetic leaflet device 800 including a pair of stabilizing arms 802 and a baffle 804 attached to the stabilizing arms 802. The stabilizing arms 802 extend in an arc, such as a semi-circle or semi-oval, and are intended to extend along the posterior atrial wall from the anterolateral commissure to the posteromedial commissure. The stabilizing arms 802 are configured to frictionally engage with the atrial wall and may be formed of a balloon expandable material such as stainless steel or a self-expanding material such as a nickel-titanium alloy (e.g., Nitinol®) having an unrestrained size which ensures engagement with the atrial wall during diastole as well as systole. The stabilizing arms 802 preferably include a plurality of cleats 806 adapted to engage tissue and assist in fixation of the prosthetic device 800. The stabilizing arms 802 may optionally be covered with a biocompatible fabric covering 810 to promote tissue in-growth.

The baffle 804 is intended displace the posterior leaflet and provide an atraumatic coaptation surface for the anterior leaflet, thereby preventing or at least inhibiting regurgitant blood flow. In some embodiments, the baffle 804 is formed of a biocompatible foam. The baffle 804 may, for example, have a teardrop shape. The posterior portion of the baffle 804 may include a plurality of frictional engagement portions or cleats 806 configured to engage with the posterior leaflet and possibly the annulus. In other embodiments, the baffle 804 may have a basket shape (like baffle 114 in FIG. 3A) enclosing a hollow interior such as described with reference to FIG. 2B. The baffle 804 extends in a downstream direction (e.g., distally) from a posterior portion of the stabilizing arms 802 and includes a plurality of struts 808 forming a somewhat convex structure covered by biocompatible covering 810 having pores to facilitate tissue in-growth. The posterior side of the baffle 804 is configured to frictionally engage one or more lobes of the posterior leaflet. The cleats 806 on the posterior portion of the baffle are not obstructed by the covering 810.

FIG. 8B shows the prosthetic leaflet device 800 with an optional strut 812 spanning the otherwise free ends of the stabilizing arm 802. The strut 812 may help ensure that the stabilizing arms stay engaged with the atrial wall. The stabilizing arm 802 is configured to extend between the anterior and posterior leaflet commissure.

In use the prosthetic leaflet device 800 is implanted with the baffle 804 straddling the annulus with part of the baffle 804 extending into the ventricle and engaging with the posterior leaflet. The stabilizing arms 802 may remain in the atrium, skirting the periphery of the annulus.

Deployment of the Prosthetic Leaflet Device

Each of the prosthetic leaflet devices disclosed herein may be delivered via a trans-septal, trans-atrial, or trans-apical approach. The implant may for example be delivered from a 3-9 mm, 4-8 mm, 5-7 mm, 3 mm, 4 mm, 5 mm, 6 mm, 7 mm, 8 mm or 9 mm inner diameter sheath with the sheath tip positioned approximately at P2. Controlled unsheathing allows the implant to expand radially in place against the annulus on the posterior side.

Some of the embodiments utilize control wires or sutures to collapse the prosthetic device for repositioning and/or re-sheathing in the catheter prior to final release and to allow for complete recovery of the implant. A circumferential cinching element may also be contained within the baffle support elements to facilitate a controlled radial expansion during deployment and to aid in radial contraction prior to complete recovery of the implant. In other embodiments, the control wire(s) and/or control arm(s) may bend the anterior portion of the atrial-fixation member inwards towards the posterior P2 portion of the atrial-fixation member upon recovery to reduce the overall diameter of the atrial-fixation member and ensure disengagement of the fictional elements from the tissue.

Several embodiments of implants in accordance with the present technology are delivered trans-septally. Prior to placement in the annulus, the prosthetic leaflet device is advanced partially out of the delivery catheter into the atrium, where it can be rotationally aligned with respect to the native valve and prepared for placement. The prosthetic leaflet device is advanced into the annulus and allowed to expand and resume its unconstrained shape, thereby engaging the annulus and the sub annular space posteriorly with frictional elements and then engaging the anterior surface of the left atrium with radial force. In one embodiment, the posterior aspect of the structural ring has an active (e.g., movable) hinge that folds radially inward during delivery and/or recovery.

In several embodiments the baffle is the first portion of the prosthetic leaflet device that is deployed. This enables the baffle to be positioned at a desired location and orientation with respect to the native valve, and in particular the posterior leaflet and the annulus in mitral valve applications. Then the posterior ventricular hook or cleats are engaged with the posterior leaflet and annulus. If the prosthetic leaflet device is equipped with trigonal extensions, then the trigonal extensions are the next portions of the prosthetic leaflet device that are deployed from the catheter. The structural ring and finally the atrial-fixation member (if present) are the last two portions of the prosthetic leaflet device to be deployed from the catheter into the left atrium.

This concept can also be applied to other valves besides the mitral valve. For example, some patients have aortic valve regurgitation due to degeneration of one of the leaflets or dilation of the aortic root. One embodiment of a device for repair of an aortic valve comprises a blocker which displaces the non-coronary cusp of the aortic valve. The ventricular surface of the blocker is shaped roughly like the ventricular surface of the non-coronary cusp in the closed position. It can be somewhat larger than the native leaflet, so that it coapts with the other leaflets of the aortic valve. The peripheral surface of the blocker can be shaped to generally conform to the shape of the non-coronary sinus. The surface which faces towards the aortic lumen can taper from the coaptation surfaces to the aortic wall 1-4 cm downstream (cranially) of the aortic valve. The blocker can be connected to a stent which is deployed in the aortic root or ascending aorta to hold it in place. As in the prior embodiments, the blocker can be formed from foam or an expanding metal or polymer framework which can be covered with expanded PTFE, pericardium, or other biocompatible tissue which forms an atraumatic coaptation surface for the other leaflets of the valve. The remaining two leaflets of the aortic valve, if they are not stenosed, should provide ample luminal area so the repaired valve does not have an excessive pressure gradient as blood flows through it.

Representative Examples

Several non-limiting yet representative examples of embodiments in accordance with the present technology are set forth in the enumerated clauses below. Representative features are set out in the following clauses, which stand alone or may be combined, in any combination, with one or more features disclosed in the text and/or drawings of the specification. When used in this specification and claims, the terms "comprises" and "comprising" and variations thereof mean that the specified features, steps or integers are included. The terms are not to be interpreted to exclude the presence of other features, steps or components. The features disclosed in the foregoing clauses, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

1. A heart valve repair device, comprising:
   an atrial-fixation member having an expandable mesh having an oval or circular shape in a deployed configuration, the atrial-fixation member defining a central lumen; and
   a baffle extending from a portion of the atrial-fixation member, the baffle having an anterior portion with a smooth, atraumatic surface for coapting with at least a portion of one or more native leaflets of a native heart valve, a posterior portion configured to engage and displace at least a portion of another native leaflet of the native heart valve, wherein the baffle extends radially inward from the atrial-fixation member into the central lumen to approximate a closed position of the displaced native leaflet.

2. The device of clause 1, wherein
   the baffle includes struts defining a basket having a hollow interior volume, the baffle further including a restraining portion for engaging and restraining at least a first portion of a functionally deficient native leaflet while leaving a second portion of the functionally deficient native leaflet mobile, the baffle extends radially inward into the central lumen to approximate a closed position for the functionally deficient leaflet.

3. The device according to any of clauses 1 or 2, further comprising a plurality of frictional elements provided on portions of the atrial-fixation member or the baffle.

4. The device according to any of clauses 1-3, wherein the medial and lateral sides of the atrial-fixation member do not include any frictional elements.

5. The device according to any of clauses 1-4, wherein the baffle comprises a basket enclosing a hollow interior.

6. The device according to any of clauses 1-5, wherein the baffle comprises plurality of anterior struts and a plurality of posterior struts with gaps interposed between adjacent ones of the anterior and posterior struts.

7. The device according to any of clauses 1-6, comprising:
   a fabric covering at least partially surrounding the baffle; and
   the basket has a mouth which is not covered by the fabric.

8. The device according to any of clauses 1-6, comprising:
   a fabric covering at least partially surrounding the baffle;
   the basket has a mouth which is covered by the fabric.

9. The device according to any of clauses 1, 3, 4, 7 or 8 wherein the baffle comprises a biocompatible foam.

10. The device according to any of clauses 1-9, wherein the anterior portion of the baffle has a convex shape.

11. The device according to any of clauses 1-10, wherein the posterior portion of the baffle is sized to engage with a central scallop a native mitral valve leaflet having three scallops, while leaving the remaining two scallops mobile.

12. The device according to any of clauses 1-11, further comprising:
   a first set of plural suture loops circumferentially disposed around the atrial-fixation member, each suture loop of the first set of suture loops having a lumen; and
   a first suture disposed in the lumen of the suture loops and interconnecting adjacent suture loops;
   wherein a diameter of the atrial-fixation member is adjusted by cinching the first suture.

13. The device according to clause 12, further comprising:
   a second set of plural suture loops circumferentially disposed around the baffle, each suture loop of the second set of suture loops having a lumen; and
   a second suture disposed in the lumen of the suture loops and interconnecting adjacent suture loops;
   wherein a diameter of the baffle is adjusted by cinching the second suture.

14. The device according to clause 13, further comprising:
   a third suture loop provided on the baffle,
   a third suture disposed in the lumen of the third suture loop;
   wherein the pulling on the third suture displaces the baffle.
15. The device according to any of clauses 1-14, further comprising at least one fabric segment of fabric attached to and at least partially spanning the atrial-fixation member, wherein the fabric covering facilitates tissue ingrowth.
16. The device according to any of clauses 1-15, further comprising at least one fabric segment of fabric depending from the distal end of the atrial-fixation member.
17. The device according to clauses 15 or 16, further comprising a biasing member attached to the at least one fabric segment and biasing the fabric segment away from the central lumen.
18. The device according to any of clauses 1-17, wherein the atrial-fixation member comprises at least two rows of cells.
19. The device according to any of clauses 1-18, wherein:
   the atrial-fixation member further comprises a row of chevrons;
   at least two of the chevrons include a through-hole; and
   a suture threaded through the through-hole;
   wherein cinching the suture adjusts a diameter of the atrial-fixation member.
20. The device according to any of clauses 1-19, wherein the atrial-fixation member has a frustoconical shape.
21. The device according to any of clauses 1-20, wherein the atrial-fixation member has a shape to engage solely with an atrial wall of the native heart valve.
22. The device according to any of clauses 1-21, wherein a size of the atrial-fixation member unconstrained by external forces is larger than a size of a native atrium in diastole.
23. The device according to any of clauses 1-22, wherein the device is fixed relative to the native cardiac valve solely by the atrial-fixation member and the baffle.
24. The device according to any of clauses 1-23, wherein the atrial fixation member has an anterior side and a posterior side, a proximal end of the anterior side of the atrial-fixation member is offset vertically from a proximal end of the posterior side of the atrial-fixation member.
25. The device according to any of clauses 1-24, wherein the atrial-fixation member has an asymmetric shape with a length of an anterior side being longer than a length of a posterior side of the atrial-fixation member such that the anterior side of the atrial-fixation member is taller in a vertical direction than the posterior side of the atrial-fixation member.
26. The device according to any of clauses 1-25, wherein a posterior side of the atrial-fixation member is stiffer than an anterior side of the atrial-fixation member.
27. The device according to clause 26, wherein the atrial-fixation member includes a plurality of interconnected struts forming plural cells, with the struts on the posterior side of the atrial-fixation member being at least one of thicker, wider and/or having narrower gaps between adjacent struts than the struts on the anterior side of the atrial-fixation member.
28. A method for repairing a regurgitant cardiac valve in a heart having an atrium having atrial walls, a ventricle having ventricular walls, a cardiac valve having at least two leaflets which have an open position and a closed position, the cardiac valve located at the boundary between the atrium and the ventricle, and an annulus surrounding the cardiac valve, the method comprising:
   providing a prosthetic leaflet device, including:
      an atrial-fixation member formed of a mesh material, the atrial-fixation member defining a central lumen configured to fluidically couple the atrium and the ventricle, the atrial-fixation member having an anterior portion, a posterior portion, a proximal end, a distal end, a medial side, and a lateral side; and
      a baffle attached to the atrial-fixation member, an anterior portion of the baffle having a smooth, atraumatic surface which acts as a prosthetic coaptation surface for one of the at least two leaflets, a posterior portion of the baffle configured to engage and displace at least a portion of another of the at least two leaflets, the baffle protruding into the central lumen and approximating the closed position of the displaced leaflet; and
   implanting the prosthetic leaflet device in the atrium such that the atrial-fixation member is spaced away from the annulus; and
   positioning the baffle to abut one of the at least two leaflets.
29. The method of clause 28, wherein:
   the atrial-fixation member of the prosthetic leaflet device includes at least two suture loops having an eyelet, a suture strand threaded through the eyelets, wherein cinching the suture strand collapses the atrial-fixation member; and
   implanting the leaflet prosthetic includes:
      cinching the suture strand to collapse the atrial-fixation member;
      placing the prosthetic leaflet device with the atrial-fixation member collapsed in the atrium; and
      uncinching the prosthetic leaflet device such that the atrial-fixation member expands into contact with the atrial walls.
30. The method of clauses 28 or 29, wherein the prosthetic leaflet device is fixed relative to the cardiac valve solely by the atrial-fixation member and the baffle.
31. A heart valve repair device, comprising:
   an atrial fixation member defining a central lumen;
   a baffle attached to the atrial fixation member, the baffle having an anterior portion with a smooth, atraumatic surface defining a prosthetic coaptation surface for coapting with at least one native leaflet of a native heart valve, and a posterior portion for engaging and displacing at least a portion of a functionally deficient leaflet, the baffle extending radially inward into the central lumen to approximate a closed position of the functionally deficient leaflet.
32. The device according to clause 31, further comprising a fabric covering at least partially surrounding the baffle.
33. The device according to clauses 31 or 32, wherein the baffle comprises a biocompatible foam.
34. The device according to any of clauses 31-33, further comprising a plurality of frictional elements provided on the atrial fixation member and on a posterior portion of the baffle, and wherein the baffle remains in at least a substantially fixed orientation with respect to the atrial fixation member.
35. The device according to clause 31, wherein the baffle comprises a basket enclosing a hollow interior.
36. The device according to clause 35, wherein the baffle comprises a plurality of anterior struts and a plurality of posterior struts with gaps interposed between adjacent ones of the anterior and posterior struts.
37. The device according to clauses 35 or 36, wherein the basket has a mouth, the basket being covered by a fabric, with the mouth of the basket being uncovered.

38. The device according to any of clauses 31-37, wherein the anterior portion of the baffle has a convex shape.

39. The device according to any of clauses 31-39, wherein the posterior portion of the baffle is sized to engage with and displace a central scallop of an anterior or a posterior mitral valve leaflet having three scallops, while leaving the remaining two scallops mobile.

40. The device according to any of clauses 31-39, wherein the posterior portion of the baffle is sized to engage with and displace the entire native leaflet.

41. The device according to any of clauses 31-40, wherein the atrial fixation member comprises a semicircular ring which extends in a first plane and the baffle extends in a second plane which is parallel and vertically offset from the first plane.

42. The device according to clause 31, wherein the anterior portion of the baffle comprises a biocompatible foam.

43. The device according to any of clauses 31-41, wherein the atrial fixation member includes a semi-circular ring sized to skirt the periphery of the annulus between an anterolateral commissure and a posteromedial commissure.

44. A heart valve repair device, comprising:
    an atrial fixation member defining a central lumen;
    at least one fixation mechanism selected from the group of a trigonal anchor system and posterior hook;
    wherein the trigonal anchor system comprises a first trigonal extension attached to the atrial fixation member and extending away from the baffle, a second trigonal extension attached to the second end of the partial ring and extending away from the baffle, and one of an anchor and an atraumatic tip attached to a terminal end of the first and second trigonal extensions;
    wherein the posterior hook is attached to a posterior portion of the atrial fixation member, and the posterior hook has a first portion which extends distally and a second portion which curves in a posterior direction, whereby the posterior hook is shaped to extend into a ventricle of a heart and engage a ventricular side of a native cardiac annulus; and
    a baffle attached to the atrial fixation member, the baffle having an anterior portion with a smooth, atraumatic surface which defines a prosthetic coaptation surface for one or more native leaflets, and a posterior portion configured to engage and displace at least a portion of a functionally deficient leaflet, the baffle extending into the central lumen and approximating a closed position for the functionally deficient leaflet.

45. The device according to clause 44, further comprising a fabric covering at least partially surrounding the baffle.

46. The device according to clauses 44 or 45, wherein the baffle comprises a biocompatible foam.

47. The device according to any of clauses 44-46, further comprising a plurality of frictional elements on the atrial fixation member and on a posterior portion of the baffle.

48. The device according to clause 44, wherein the baffle comprises a basket enclosing a hollow interior.

49. The device according to clause 48, wherein the baffle comprises a plurality of anterior struts and a plurality of posterior struts with gaps interposed between adjacent ones of the anterior and posterior struts.

50. The device according to clauses 48 or 49, wherein the basket has a mouth, the basket being covered by a fabric, with the mouth of the basket being uncovered.

51. The device according to any of clauses 44-50, wherein the anterior portion of the baffle has a convex shape.

52. The device according to any of clauses 44-51, wherein the posterior portion of the baffle is sized and configured to engage with and displace a central scallop of an anterior or a posterior mitral valve leaflet having three scallops, while leaving the remaining two scallops mobile.

53. The device according to any of clauses 44-52, wherein the posterior portion of the baffle is sized to engage with the entire functionally deficient leaflet.

54. The device according to any of clauses 44-53, wherein the atrial fixation member includes a semi-circular ring sized to skirt the periphery of the native cardiac annulus between an anterolateral commissure and a posteromedial commissure.

55. A heart valve repair device, comprising:
    an atrial-fixation member defining a central lumen; and
    a baffle attached to the atrial-fixation member, the baffle having an anterior portion with a smooth, atraumatic surface which defines a coaptation surface for engaging one or more native leaflets, and a posterior portion engaging and displacing at least a portion of a functionally deficient leaflet, the baffle extending into the central lumen to approximate a closed position for the functionally deficient leaflet.

56. The device of clause 55, further comprising a fabric covering at least partially surrounding the baffle.

57. The device of clauses 55 or 56, wherein the baffle comprises a biocompatible foam.

58. The device of any of clauses 55-57, further comprising a plurality of frictional engagement elements on the atrial-fixation member and the posterior portion of the baffle.

59. The device according to any of clauses 55, 56 or 58, wherein the baffle comprises a basket enclosing a hollow interior.

60. The device according to any of clauses 55, 56, 58 or 59, wherein the baffle comprises a plurality of anterior struts and a plurality of posterior struts with gaps interposed between adjacent ones of the anterior and posterior struts.

61. The device according to any of clauses 55, 56, 58 or 59, wherein the basket has a mouth, the basket being covered by a fabric, with the mouth of the basket being uncovered.

62. The device according to any of clauses 55-61, wherein the anterior portion of the baffle has a convex shape.

63. The device according to any of clauses 55-62, wherein the posterior portion of the baffle is sized to engage with and displace a central scallop of an anterior or a posterior mitral valve leaflet having three scallops, while leaving the remaining two scallops mobile.

64. The device according to any of clauses 55-63, wherein the atrial fixation member includes a partially-circular, frustoconical shaped member having first and second ends, and a brace extending between the first and second ends of the atrial-fixation member.

65. The device according to any of clauses 55-64, further comprising at least one fixation mechanism selected from the group of a trigonal anchor and a posterior hook, wherein the trigonal anchor comprises a first trigonal extension attached to the first end of the atrial-fixation member and extending away from the baffle, a second trigonal extension attached to the second end of the atrial-fixation member and extending away from the baffle, and one of an anchor and an atraumatic tip attached to a terminal end of the first and second trigonal extensions.

66. A heart valve repair device for repairing a mitral valve having an anterior leaflet and a posterior leaflet, comprising:
    an atrial-fixation member having a collapsed configuration and an expanded configuration, the atrial-fixation member having an expandable ring-shaped mesh, and the atrial-fixation member being shaped to contact tissue of an atrial wall upstream of a native valve annulus; and a baffle extending radially inwardly from the atrial-fixation member, the baffle having an outer portion shaped to displace the posterior leaflet toward a ventricular wall and restrain the posterior leaflet in an open position, an inner portion having a coaptation surface radially inward of the outer portion, wherein the inner portion is spaced apart from the outer portion by a distance such that the coaptation surface is positioned at least proximate a closed position of the anterior leaflet.

67. The heart valve repair device of clause 66, wherein the atrial-fixation member is shaped to contact only atrial wall tissue above the native valve annulus.

68. The heart valve repair device of clauses 66 or 67, further comprising a biocompatible covering on a surface of the baffle.

69. The heart valve repair device of any of clauses 66-68, wherein the baffle comprises posterior struts extending in a downstream direction from the atrial-fixation member and anterior struts projecting inwardly and upwardly from a downstream end of the posterior struts, and wherein the heart valve repair device further includes a covering attached to the posterior and anterior struts.

70. The heart valve repair device of any of clauses 66-69, wherein the atrial-fixation member comprises a plurality of struts, and wherein the heart valve repair device further includes a covering attached to the struts of the atrial-fixation member.

We claim:

1. A heart valve repair device, comprising:
   an atrial-fixation member; and
   a baffle extending from a portion of the atrial-fixation member, the baffle having an anterior portion configured to coapt with at least a portion of one or more first native valve leaflets of a native heart valve, and a posterior portion configured to (a) displace a first portion of a second native valve leaflet of the native heart valve while (b) leaving a remaining second portion of the second native valve leaflet mobile, wherein the baffle encloses a hollow volume.

2. The heart valve repair device of claim 1 wherein the atrial-fixation member is configured to contact an atrial wall upstream of an annulus of the native heart valve.

3. The heart valve repair device of claim 2 wherein the atrial-fixation member is configured to span only partially circumferentially about the atrial wall.

4. The heart valve repair device of claim 1 wherein the atrial-fixation member is configured to contact an atrial wall upstream of an annulus of the native heart valve, wherein the atrial-fixation member spans only partially circumferentially about an anterior portion of the atrial wall, and wherein the atrial-fixation member is connected to the baffle by two or more struts.

5. The heart valve repair device of claim 1 wherein the baffle is configured to project radially inward toward a central axis of the native heart valve to approximate a closed position of the first portion of the second native valve leaflet.

6. The heart valve repair device of claim 1, further comprising a hook extending from the posterior portion of the baffle and configured to engage at least one of a ventricular side of an annulus of the native heart valve, a posterior ventricular wall proximate to the native heart valve, and the second native leaflet.

7. The heart valve repair device of claim 1 wherein the native heart valve is a native mitral valve, wherein the one or more first native leaflets comprise a native anterior leaflet of the native mitral valve, wherein the second native leaflet comprises a native posterior leaflet of the native mitral valve, wherein the native posterior leaflet includes three scallops, wherein the anterior portion of the baffle is configured to coapt with a portion of the native anterior leaflet, and wherein the posterior portion of the baffle is configured to displace a central one of the scallops of the native posterior leaflet.

8. The heart valve repair device of claim 7 wherein the atrial-fixation member is configured to contact an atrial wall upstream of an annulus of the native mitral valve, and wherein the atrial-fixation member is configured to span only partially circumferentially about the atrial wall above the native anterior leaflet.

9. The heart valve repair device of claim 1 wherein the first portion of the second native valve leaflet is a central portion, and wherein the second portion of the second native valve leaflet is a side portion.

10. The heart valve repair device of claim 1 wherein the second native valve leaflet includes a central scallop and a pair of side scallops, wherein the first portion of the second native valve leaflet comprises at least a portion of the central scallop, and wherein the second portion of the second native valve leaflet comprises at least a portion of the pair of side scallops.

11. A heart valve repair device, comprising:
    an atrial-fixation member; and
    a baffle extending from a portion of the atrial-fixation member, the baffle having an anterior portion configured to coapt with at least a portion of one or more first native valve leaflets of a native heart valve, and a posterior portion configured to (a) displace a first portion of a second native valve leaflet of the native heart valve while (b) leaving a remaining second portion of the second native valve leaflet mobile, wherein the baffle comprises a plurality of struts defining a hollow volume.

12. The heart valve repair device of claim 11 wherein the plurality of struts includes a plurality of anterior struts and a plurality of posterior struts with gaps interposed between adjacent ones of the anterior and posterior struts.

13. The heart valve repair device of claim 11 wherein the baffle further comprises a covering attached to the struts and enclosing the hollow volume.

14. A heart valve repair device, comprising:
    an atrial-fixation member; and
    a baffle extending from a portion of the atrial-fixation member, the baffle having an anterior portion configured to coapt with at least a portion of one or more native leaflets of a native heart valve, and a posterior portion configured to displace at least a portion of another native leaflet of the native heart valve, wherein the baffle comprises a plurality of anterior struts and a plurality of posterior struts with gaps interposed between adjacent ones of the anterior and posterior struts.

15. The heart valve repair device of claim 14 wherein the atrial-fixation member is configured to contact an atrial wall upstream of an annulus of the native heart valve.

16. The heart valve repair device of claim 15 wherein the atrial-fixation member spans only partially circumferentially about the atrial wall.

17. The heart valve repair device of claim 14 wherein the native heart valve is a native mitral valve having a native anterior leaflet and a native posterior leaflet, wherein the anterior portion of the baffle is configured to coapt with a portion of the native anterior leaflet, and wherein the posterior portion of the baffle is configured to displace a portion of the posterior leaflet.

18. The heart valve repair device of claim 17 wherein the atrial-fixation member is configured to contact an atrial wall upstream of an annulus of the native mitral valve, and wherein the atrial-fixation member is configured to span only partially circumferentially about the atrial wall above the native anterior leaflet.

19. The heart valve repair device of claim 14 wherein the baffle is configured to project radially inward toward a central axis of the native heart valve to approximate a closed position of the displaced native leaflet.

20. The heart valve repair device of claim 14 wherein the atrial-fixation member is configured to contact an atrial wall upstream of an annulus of the native heart valve, wherein the atrial-fixation member spans only partially circumferentially about an anterior portion of the atrial wall, and wherein the atrial-fixation member is connected to the baffle by two or more struts.

21. A heart valve repair device, comprising:
an atrial-fixation member extending at least partially around a vertical axis;
a baffle extending downward from a portion of the atrial-fixation member relative to the vertical axis, the baffle having an anterior portion configured to coapt with at least a portion of one or more native leaflets of a native heart valve, and a posterior portion configured to displace at least a portion of another native leaflet of the native heart valve, wherein the anterior portion is configured to remain fixed in position relative to the vertical axis throughout a cardiac cycle of the native heart valve, wherein the baffle encloses a hollow volume;
a plurality of suture loops circumferentially disposed around the atrial-fixation member, each suture loop having a lumen; and
a suture extending through the lumens of the suture loops, wherein a diameter of the atrial-fixation member is adjustable by cinching the suture.

22. The heart valve repair device of claim 21 wherein the atrial-fixation member is configured to contact an atrial wall upstream of an annulus of the native heart valve.

23. The heart valve repair device of claim 22 wherein the atrial-fixation member spans only partially circumferentially about the atrial wall.

24. The heart valve repair device of claim 21 wherein the native heart valve is a native mitral valve having a native anterior leaflet and a native posterior leaflet, wherein the anterior portion of the baffle is configured to coapt with a portion of the native anterior leaflet, and wherein the posterior portion of the baffle is configured to displace a portion of the posterior leaflet.

25. The heart valve repair device of claim 24 wherein the atrial-fixation member is configured to contact an atrial wall upstream of an annulus of the native mitral valve, and wherein the atrial-fixation member is configured to span only partially circumferentially about the atrial wall above the native anterior leaflet.

26. The heart valve repair device of claim 21 wherein the baffle is configured to project radially inward toward a central axis of the native heart valve to approximate a closed position of the displaced native leaflet.

\* \* \* \* \*